(12) United States Patent
Prescott et al.

(10) Patent No.: US 7,488,316 B2
(45) Date of Patent: Feb. 10, 2009

(54) CONTROL OF DRUG RELEASE BY TRANSIENT MODIFICATION OF LOCAL MICROENVIRONMENTS

(75) Inventors: James H. Prescott, Cambridge, MA (US); Timothy Kreiger, Houston, TX (US); Elizabeth R. Proos, Uxbridge, MA (US)

(73) Assignee: MicroCHIPS, Inc., Bedford, MA (US)

( * ) Notice: Subject to any disclaimer, the term of this patent is extended or adjusted under 35 U.S.C. 154(b) by 0 days.

(21) Appl. No.: 11/339,062

(22) Filed: Jan. 25, 2006

(65) Prior Publication Data

US 2006/0171989 A1 Aug. 3, 2006

Related U.S. Application Data

(60) Provisional application No. 60/760,129, filed on Jan. 18, 2006, provisional application No. 60/646,913, filed on Jan. 25, 2005.

(51) Int. Cl.
| | |
|---|---|
| A61K 9/22 | (2006.01) |
| A61K 38/00 | (2006.01) |
| A61K 38/22 | (2006.01) |
| A61F 2/00 | (2006.01) |
| B23K 31/02 | (2006.01) |

(52) U.S. Cl. .................. 604/890.1; 424/426; 514/12; 228/124.6

(58) Field of Classification Search .............. 604/890.1, 604/891.1; 228/110.1; 514/12; 228/124.6; 424/426
See application file for complete search history.

(56) References Cited

U.S. PATENT DOCUMENTS

| | | | |
|---|---|---|---|
| 3,952,741 A | 4/1976 | Baker | |
| 4,012,496 A | 3/1977 | Schopflin et al. | |
| 4,146,029 A | 3/1979 | Ellinwood, Jr. | |
| 4,360,019 A | 11/1982 | Portner et al. | |
| 4,416,659 A | 11/1983 | Simpson et al. | |
| 4,507,115 A | 3/1985 | Kambara et al. | |
| 4,585,652 A | 4/1986 | Miller et al. | |
| 4,659,696 A | 4/1987 | Hirai et al. | |
| 4,698,328 A | 10/1987 | Neer et al. | |
| 4,793,825 A | 12/1988 | Benjamin et al. | |
| 4,822,616 A | 4/1989 | Zimmermann et al. | |
| 4,833,125 A | 5/1989 | Neer et al. | |
| 4,917,685 A | 4/1990 | Viswanathan et al. | |
| 4,957,494 A | 9/1990 | Wong et al. | |
| 4,994,023 A | 2/1991 | Wellinghoff et al. | |
| 5,041,107 A | 8/1991 | Heil, Jr. | |
| 5,042,975 A | 8/1991 | Chien et al. | |
| 5,252,294 A | 10/1993 | Kroy et al. | |
| 5,262,127 A | 11/1993 | Wise et al. | |
| 5,317,010 A | 5/1994 | Pang et al. | |
| 5,318,557 A | 6/1994 | Gross | |
| 5,366,454 A | 11/1994 | Currie et al. | |
| 5,368,704 A | 11/1994 | Madou et al. | |
| 5,385,709 A | 1/1995 | Wise et al. | |
| 5,393,533 A | 2/1995 | Versic | |
| 5,427,585 A | 6/1995 | Bettinger | |
| 5,429,822 A | 7/1995 | Gresser et al. | |
| 5,443,508 A | 8/1995 | Giampapa | |
| 5,474,527 A | 12/1995 | Bettinger | |
| 5,490,962 A | 2/1996 | Cima et al. | |
| 5,496,801 A * | 3/1996 | Holthuis et al. ............... | 514/12 |
| 5,499,979 A | 3/1996 | Wong et al. | |
| 5,510,138 A | 4/1996 | Sanftleben et al. | |
| 5,510,370 A | 4/1996 | Hock | |
| 5,533,995 A | 7/1996 | Corish et al. | |
| 5,605,662 A | 2/1997 | Heller et al. | |
| 5,660,846 A | 8/1997 | Cheikh | |
| 5,670,514 A | 9/1997 | Audia et al. | |
| 5,782,799 A | 7/1998 | Jacobsen et al. | |
| 5,797,898 A | 8/1998 | Santini, Jr. et al. | |
| 5,824,204 A | 10/1998 | Jerman | |
| 5,824,646 A | 10/1998 | Fujii et al. | |
| 5,837,276 A | 11/1998 | Cheikh | |
| 5,843,767 A | 12/1998 | Beattie | |
| 5,891,108 A | 4/1999 | Leone et al. | |
| 5,893,974 A | 4/1999 | Keller et al. | |
| 5,938,923 A | 8/1999 | Tu et al. | |
| 5,945,412 A | 8/1999 | Fuh et al. | |
| 5,962,081 A | 10/1999 | Öhman et al. | |

(Continued)

FOREIGN PATENT DOCUMENTS

| | | |
|---|---|---|
| DE | 39 08 822 A1 | 3/1989 |
| DE | 197 16 683 C1 | 6/1998 |
| WO | 8606488 A1 | 11/1986 |
| WO | WO 93/03790 A1 | 3/1993 |
| WO | WO 02/056862 A2 | 7/2002 |
| WO | WO 03/024355 A1 | 3/2003 |

OTHER PUBLICATIONS

Becker, et al., "*Polymer microfabrication methods for microfluidic analytical methods*," Electrophoresis. 21:12-26 (2000).

(Continued)

*Primary Examiner*—Maryam Monshipouri
*Assistant Examiner*—Marsha M Tsay
(74) *Attorney, Agent, or Firm*—Sutherland Asbill & Brennan LLP

(57) ABSTRACT

Methods, formulations, and devices are provided for enhancing drug delivery from a medical device. The method is provided for increasing the rate or quantity of a drug formulation released from an implantable drug delivery device, which method comprises the step of providing a release-modifying agent within or proximate to the implantable drug delivery device, in a manner effective to inhibit gelation, aggregation, or precipitation of the drug formulation being released from the device. The drug formulation and the release-modifying agent may be stored together in at least one reservoir in the implantable drug deliver device. Alternatively, the release-modifying agent may be stored in one or more reservoirs separate from the drug formulation.

43 Claims, 7 Drawing Sheets

U.S. PATENT DOCUMENTS

| | | |
|---|---|---|
| 5,976,101 A | 11/1999 | Sibalis |
| 5,976,336 A | 11/1999 | Dubrow et al. |
| 5,981,489 A | 11/1999 | Stevenson et al. |
| 5,985,328 A | 11/1999 | Chu et al. |
| 5,989,445 A | 11/1999 | Wise et al. |
| 6,001,090 A | 12/1999 | Lenhart |
| 6,010,492 A | 1/2000 | Jacobsen et al. |
| 6,011,011 A | 1/2000 | Hageman et al. |
| 6,042,710 A | 3/2000 | Dubrow |
| 6,047,214 A | 4/2000 | Mueller et al. |
| 6,051,686 A | 4/2000 | Krstenansky et al. |
| 6,056,734 A | 5/2000 | Jacobsen et al. |
| 6,062,461 A | 5/2000 | Sparks et al. |
| 6,066,163 A | 5/2000 | John |
| 6,071,305 A | 6/2000 | Brown et al. |
| 6,081,736 A | 6/2000 | Colvin et al. |
| 6,083,763 A | 7/2000 | Balch |
| 6,096,070 A | 8/2000 | Ragheb et al. |
| 6,114,658 A | 9/2000 | Roth et al. |
| 6,123,861 A | 9/2000 | Santini, Jr. et al. |
| 6,140,740 A | 10/2000 | Porat et al. |
| 6,142,972 A | 11/2000 | Cheikh |
| 6,160,084 A | 12/2000 | Langer et al. |
| 6,163,720 A | 12/2000 | Gyory et al. |
| 6,171,850 B1 | 1/2001 | Nagle et al. |
| 6,221,024 B1 | 4/2001 | Miesel |
| 6,232,150 B1 | 5/2001 | Lin et al. |
| 6,237,398 B1 | 5/2001 | Porat et al. |
| 6,239,144 B1 | 5/2001 | Galvin et al. |
| 6,241,762 B1 | 6/2001 | Shanley |
| 6,248,540 B1 | 6/2001 | Weinberg et al. |
| 6,251,688 B1 | 6/2001 | Erb et al. |
| 6,261,584 B1 | 7/2001 | Peery et al. |
| 6,264,990 B1 | 7/2001 | Knepp et al. |
| 6,273,908 B1 | 8/2001 | Ndondo-Lay |
| 6,273,913 B1 | 8/2001 | Wright et al. |
| 6,284,730 B1 | 9/2001 | Dietrich et al. |
| 6,287,628 B1 | 9/2001 | Hossainy et al. |
| 6,288,888 B1 | 9/2001 | Sakata et al. |
| 6,294,390 B1 | 9/2001 | Barnard et al. |
| 6,306,420 B1 | 10/2001 | Cheikh |
| 6,331,439 B1 | 12/2001 | Cherukuri et al. |
| 6,334,859 B1 | 1/2002 | Richter |
| 6,340,421 B1 | 1/2002 | Vachon et al. |
| 6,349,232 B1 | 2/2002 | Gordon |
| 6,366,794 B1 | 4/2002 | Moussy et al. |
| 6,376,477 B2 | 4/2002 | Schmidt et al. |
| 6,387,711 B1 | 5/2002 | Sundaram et al. |
| 6,388,043 B1 | 5/2002 | Langer et al. |
| 6,395,326 B1 | 5/2002 | Castro et al. |
| 6,417,333 B1 | 7/2002 | Bringhurst et al. |
| 6,436,853 B2 | 8/2002 | Lin et al. |
| 6,483,368 B2 | 11/2002 | Mayer et al. |
| 6,484,045 B1 | 11/2002 | Holker et al. |
| 6,491,666 B1 | 12/2002 | Santini, Jr. et al. |
| 6,497,729 B1 | 12/2002 | Moussy et al. |
| 6,512,939 B1 | 1/2003 | Colvin et al. |
| 6,520,326 B2 | 2/2003 | McIvor et al. |
| 6,520,936 B1 | 2/2003 | Mann |
| 6,527,762 B1 | 3/2003 | Santini, Jr. et al. |
| 6,533,798 B2 | 3/2003 | Greenberg et al. |
| 6,537,250 B1 | 3/2003 | Kriesel |
| 6,537,256 B2 | 3/2003 | Santini, Jr. et al. |
| 6,541,450 B1 | 4/2003 | Barbier et al. |
| 6,551,838 B2 | 4/2003 | Santini, Jr. et al. |
| 6,558,321 B1 | 5/2003 | Burd et al. |
| 6,558,422 B1 | 5/2003 | Baker et al. |
| 6,564,807 B1 | 5/2003 | Schulman et al. |
| 6,571,125 B2 | 5/2003 | Thompson |
| 6,572,531 B2 | 6/2003 | Zilberman et al. |
| 6,590,081 B1 | 7/2003 | Zhang |
| 6,638,302 B1 | 10/2003 | Curcio et al. |
| 6,656,162 B2 | 12/2003 | Santini, Jr. et al. |
| 6,663,615 B1 | 12/2003 | Madou et al. |
| 6,669,683 B2 | 12/2003 | Santini, Jr. et al. |
| 6,702,857 B2 | 3/2004 | Brauker et al. |
| 6,709,379 B1 | 3/2004 | Brandau et al. |
| 6,730,072 B2 | 5/2004 | Shawgo et al. |
| 6,740,333 B2 | 5/2004 | Beckett et al. |
| 6,741,877 B1 | 5/2004 | Shults et al. |
| 6,773,429 B2 | 8/2004 | Sheppard, Jr. et al. |
| 6,783,543 B2 | 8/2004 | Jang |
| 6,808,522 B2 | 10/2004 | Richards et al. |
| 6,827,250 B2 | 12/2004 | Uhland et al. |
| 6,849,463 B2 | 2/2005 | Santini, Jr. et al. |
| 6,875,208 B2 | 4/2005 | Santini, Jr. et al. |
| 2002/0022826 A1 | 2/2002 | Reynolds et al. |
| 2002/0025929 A1 | 2/2002 | Sato |
| 2002/0038146 A1 | 3/2002 | Harry |
| 2002/0072734 A1 | 6/2002 | Liedtke |
| 2002/0072784 A1 | 6/2002 | Sheppard, Jr. et al. |
| 2002/0099359 A1 | 7/2002 | Santini, Jr. et al. |
| 2002/0107470 A1 | 8/2002 | Richards et al. |
| 2002/0107505 A1 | 8/2002 | Holiaday |
| 2002/0111658 A1 | 8/2002 | Greenberg et al. |
| 2002/0138067 A1 | 9/2002 | Sheppard, Jr. et al. |
| 2002/0151776 A1 | 10/2002 | Shawgo et al. |
| 2002/0161352 A1 | 10/2002 | Lin et al. |
| 2002/0183721 A1 | 12/2002 | Santini, Jr. et al. |
| 2002/0187260 A1 | 12/2002 | Sheppard, Jr. et al. |
| 2002/0188282 A1 | 12/2002 | Greenburg |
| 2003/0010808 A1 | 1/2003 | Uhland et al. |
| 2003/0032946 A1 | 2/2003 | Fishman |
| 2003/0055344 A1 | 3/2003 | Eigler et al. |
| 2003/0055345 A1 | 3/2003 | Eigler et al. |
| 2003/0069560 A1 | 4/2003 | Adamis et al. |
| 2003/0104590 A1 | 6/2003 | Santini, Jr. et al. |
| 2003/0105455 A1 | 6/2003 | Santini, Jr. et al. |
| 2003/0178403 A1 | 9/2003 | Lemmerhirt et al. |
| 2004/0034332 A1 | 2/2004 | Uhland |
| 2004/0043042 A1 | 3/2004 | Johnson et al. |
| 2004/0073137 A1 | 4/2004 | Lloyd et al. |
| 2004/0082937 A1 | 4/2004 | Ausiello et al. |
| 2004/0106914 A1 | 6/2004 | Coppeta et al. |
| 2004/0106953 A1 | 6/2004 | Yomtov et al. |
| 2004/0121486 A1 | 6/2004 | Uhland et al. |
| 2004/0127942 A1 | 7/2004 | Yomtov et al. |
| 2004/0143236 A1 | 7/2004 | Santini, Jr. et al. |
| 2004/0147905 A1 | 7/2004 | Krumme |
| 2004/0166140 A1 | 8/2004 | Santini, Jr. et al. |
| 2004/0193144 A1 | 9/2004 | Krumme |
| 2004/0247671 A1 | 12/2004 | Prescott et al. |
| 2004/0248320 A1 | 12/2004 | Santini, Jr. et al. |
| 2004/0265354 A1 | 12/2004 | Ameri et al. |
| 2005/0050859 A1 | 3/2005 | Coppeta et al. |
| 2005/0055014 A1 | 3/2005 | Coppeta et al. |
| 2005/0077584 A1 | 4/2005 | Polito et al. |
| 2005/0096587 A1 | 5/2005 | Santini, Jr. et al. |
| 2005/0143715 A1 | 6/2005 | Santini, Jr. et al. |

OTHER PUBLICATIONS

Edelman, et al., "Optimization of release from magnetically controlled polymeric drug release devices," *Biomaterials* 14(8):621-26 (1993).

Haller, et al., "Escaping the Interstitial Matrix with Enzyme-Mediated Drug Delivery," *Drug Delivery Technology*, 5(5)40-44.

Haroun, et al., "Local Drug Delivery," *Curr. Opin. Oncol.* 12(3): 187-93 (2000) (abstract only).

Kwon, et al., "Electrically Erodible Polymer Gel For Controlled Release of Drugs," Nature 354: 291-93 (1991).

Peterman, et al., "*Localized Chemical Release from an Artificial Synapse Chip*," PNAS 101(27): 9951-9954 (Jul. 6, 2004) www.pnas.org/cgi/doi/10.1073/pnas.0402089101.

Santini, et al., "Microchip Technology in Drug Delivery," *Ann. Med.* 32(6) 377-79 (2000).

Santini, et al., "A Controlled-Release Microchip," *Nature* 397(6717): 335-38 (1999).

Schaefer, *Novartis Found. Symp.* 2000; 227:225-39 (abstract).

Tierney, et al., *"New Electrorelease Systems Based on Microporous Membranes,"* J. Electrochem. Soc., 137:3789-3793 (1990).

PCT IPER for PCT/US2005/031501.

* cited by examiner

- LOCAL ENVIRONMENT
- MODIFIED LOCAL ENVIRONMENT
- DRUG FORMULATION
- RELEASE MODIFYING AGENT

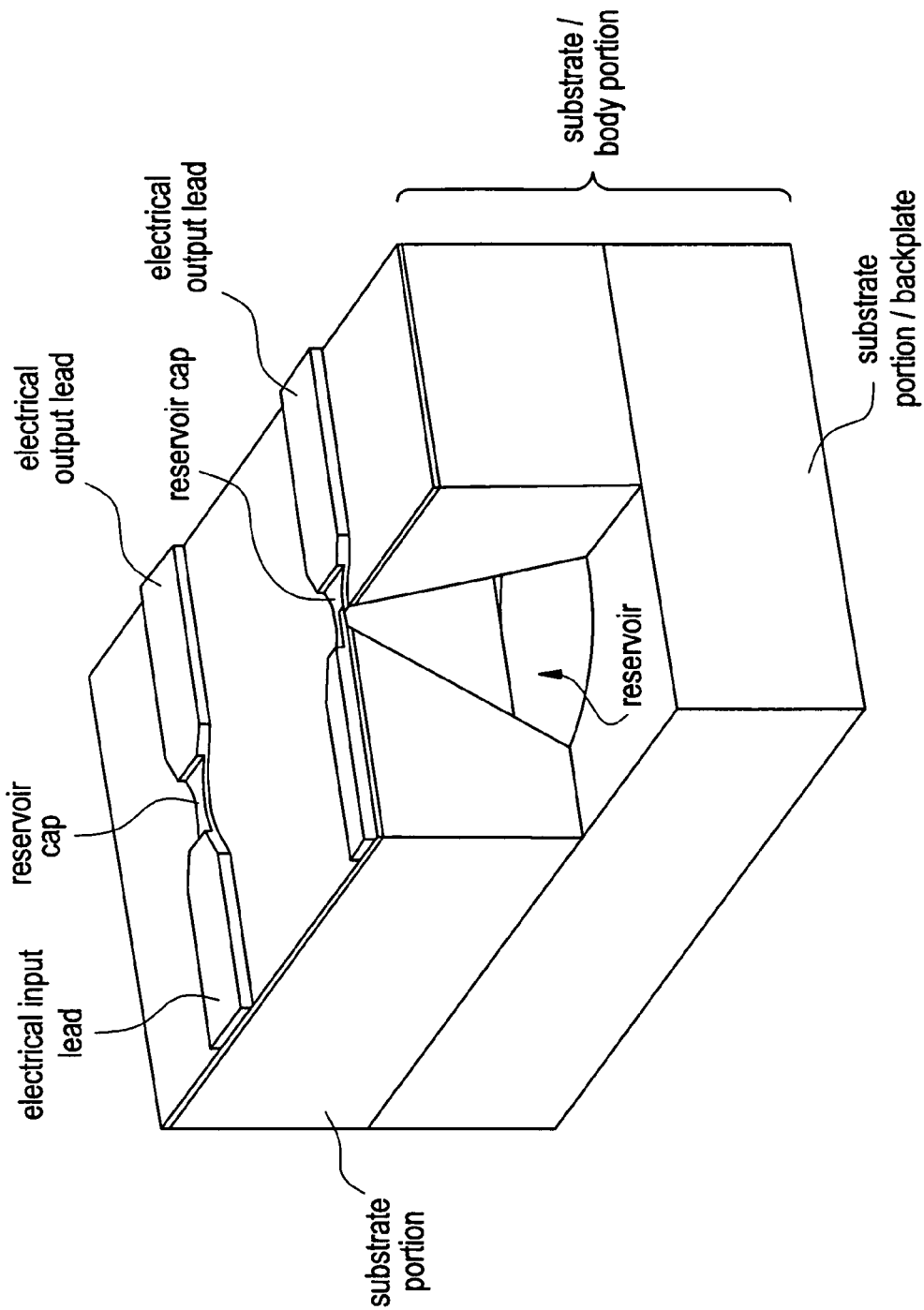

CONTROL OF DRUG RELEASE BY TRANSIENT MODIFICATION OF LOCAL MICROENVIRONMENTS

CROSS-REFERENCE TO RELATED APPLICATIONS

This application claims benefit under 35 U.S.C. § 119(e) of U.S. Provisional Application No. 60/646,913, filed Jan. 25, 2005, and U.S. Provisional Application No. 60/760,129, filed Jan. 18, 2006, which are incorporated herein by reference.

BACKGROUND OF THE INVENTION

This invention is generally in the field of (micro)containment/controlled release or exposure devices, and more particularly to implantable medical devices for the storage and controlled exposure or release of contents located in reservoirs in these devices, and applications therefor.

Undesirably, some drugs have limited solubility or undergo gelation at physiological pH. Certain phase changes of drugs can impede release from highly concentrated dosages. Such phase changes can be particularly problematic when controlling drug delivery in microenvironments. Examples of controlled delivery of drugs or other chemicals to microenvironments from implantable medical devices having microreservoirs is described in U.S. Pat. No. 5,797,898, U.S. Pat. No. 6,527,762, and U.S. Pat. No. 6,491,666, and U.S. Patent Application Publication No. 2004/0247671, all of which are incorporated by reference herein. In particular, certain types of drug formulations, such as concentrated lyophilized dosages and concentrated organic solvent solutions, tend to gel at the reservoir opening when exposed to physiological fluid and block, impede, or otherwise interfere with the release of drug from the implantable medical devices. For certain drugs this gelation is due to its limited solubility at physiological pH. For example, teriparatide, which is hPTH (1-34), has a limited solubility at physiological pH. Thus, when teriparatide is released from a drug delivery device and contacts physiological fluid, there is the potential for a precipitate or gel to form and adversely affect the drug's release.

It would be desirable to eliminate or compensate for unwanted gelation, aggregation, or precipitation of drugs or otherwise increase the delivery rate of the drugs so that drug release from reservoirs or other microcontainment devices is unimpeded and can properly controlled. In many instances, solid dosage forms are desired for their stability. It would further be desirable to improve delivery of drug formulations, particularly protein drugs, from implanted medical devices, particularly where the drug is stored in the devices as a solid or in concentrated, rather than dilute, solutions. It would also be desirable to decrease the time required for substantially all of a dose of a drug formulation to be released from a drug delivery device, where the drug is one requiring rapid delivery.

SUMMARY OF THE INVENTION

Methods, formulations, and devices are provided for enhancing drug delivery from a medical device. In one aspect, a method is provided for increasing the rate or quantity of a drug formulation released from an implantable drug delivery device, which method comprises the step of providing a release-modifying agent within or proximate to the implantable drug delivery device, in a manner effective to inhibit gelation, aggregation, or precipitation of the drug formulation being released from the device. The drug formulation and the release-modifying agent may be stored together in at least one reservoir in the implantable drug deliver device. Alternatively, the release-modifying agent may be stored in one or more reservoirs separate from the drug formulation.

The release-modifying agent may operate by altering a chemical or physical property of the physiological environment within or proximate to a reservoir from which the drug formulation is released from the device, or it may operate by altering a chemical or physical property of the drug formulation. For instance, the release-modifying agent may enhance release of the drug formulation from the device to the physiological environment, having a first pH, in which the device is implanted by imparting a second pH to at least a portion of the physiological environment within or proximate to the device where the drug formulation is stored and/or released, the second pH being less than or greater than the first pH. In other examples, the release-modifying agent may enhance release of the drug formulation to the physiological environment by (i) altering the hydrophobic or hydrophilic nature of the physiological environment within or proximate to said at least one reservoir having the drug formulation, (ii) binding to hydrophobic or hydrophilic domains of the drug formulation, or (iii) inhibiting oxidation of the drug formulation in the physiological environment.

In one embodiment, the drug formulation comprises an amino acid, a peptide, or a protein. In one example, the drug formulation comprises human parathyroid hormone or an analog thereof. In other examples, the drug formulation comprises a leutenizing hormone-releasing hormone, a gonadotropin-releasing hormone, a natriuretic peptide, exenatide, pramlintide, a tumor necrosis factor (TNF) inhibitor, an analog thereof, or a combination thereof.

The release-modifying agent may be selected from cosolvents, viscosity modifiers, chaotropic agents, polymers, salts, polymeric salts, surfactants, acids, bases, polymeric acids, polymeric bases, and combinations thereof. In one embodiment, the release-modifying agent comprises at least one non-volatile, monoprotic or polyprotic organic acid. In another embodiment, the release-modifying agent comprises at least one non-volatile, mono- or poly-functional base. A preferred release-modifying agent comprises citric acid.

In one embodiment, the implantable drug delivery device comprises one or more discrete microreservoirs. In one embodiment, the drug formulation is stored in and released from a plurality of discrete reservoirs provided in an array on a surface of the implantable drug deliver device. In one embodiment, the volume of each reservoir is between 1 nL and 500 µL.

In another aspect, an implantable medical device is provided for the storage and controlled release of a drug formulation. In one embodiment, the device comprises: a body portion; at least one reservoir located in at least one surface of the body portion and having at least one release opening; at least one drug formulation, which comprises at least one drug, disposed within the at least one reservoir; and a release-modifying agent disposed within the at least one of the reservoirs or within one or more second reservoirs. In one embodiment, the device may further include at least one reservoir cap closing off the release opening; and activation means for selectively disintegrating the reservoir cap to permit release of the drug formulation from the at least one reservoir. Preferably, the activation means for selectively disintegrating the reservoir cap comprises electrical circuits, a power source, and a controller for disintegrating the reservoir caps by electrothermal ablation.

In one embodiment, the drug formulation and the release-modifying agent are both stored in the same at least one reservoir. In one variation, the drug formulation comprises a solid matrix that has pores or interstices. In another variation, the device further includes one or more excipient materials, wherein the release-modifying agent and the one or more excipients materials are located in the pores or interstices of the solid matrix. One or more of the excipient materials may be in solid form. In one embodiment, the one or more excipient materials may include a polyethylene glycol or another polymeric material. The release-modifying agent may be located in the pores or interstices of the solid matrix. The release-modifying agent may enhance release of the drug formulation into a physiological liquid by increasing the capillary action of the physiological liquid through the matrix solid or by causing the solid matrix to be crystalline. In one particular variation, the release-modifying agent may be provided in the at least one reservoir in the form of one or more first layers and the drug formulation is provided in the at least one reservoir in the form of one or more second layers adjacent to and/or interspersed with the one or more first layers. In another embodiment, the drug formulation and the release-modifying agent are in the form of a molten solution or suspension.

In another embodiment, the release-modifying agent is stored in the one or more second reservoirs, separate from the drug formulation.

In some embodiments, the release-modifying agent enhances release of the drug formulation from said at least one reservoir to the physiological environment by inhibiting gelation, aggregation, or precipitation of the drug formulation. In one embodiment, the physiological environment has a first pH, and wherein the release-modifying agent enhances release of the drug formulation from said at least one reservoir to the physiological environment by imparting a second pH to at least a portion of the physiological environment within or proximate to the at least one reservoir having the drug formulation, the second pH being less than or greater than the first pH. In other embodiments, the release-modifying agent enhances release of the drug formulation from said at least one reservoir to the physiological environment by (i) altering the hydrophobic or hydrophilic nature of the physiological environment within or proximate to said at least one reservoir having the drug formulation, (ii) binding to hydrophobic or hydrophilic domains of the drug formulation, or (iii) inhibiting oxidation of the drug formulation in the physiological environment.

In one embodiment, the at least one reservoir further includes a polyethylene glycol or another back-fill material.

In another embodiment, the drug formulation is sealed in the at least one reservoir at a reduced pressure, relative to ambient pressure, or with an inert gas, or both at a reduced pressure and with an inert gas.

In a preferred embodiment, the at least one reservoir is a microreservoir. In another embodiment, the device has a plurality of discrete reservoirs provided in an array on a surface of the body portion and containing the drug formulation. In various embodiments, the body portion is in the form of a chip, a disk, a tube, or a sphere. The body portion may be made of silicon, a metal, a polymer, a ceramic, or a combination thereof.

BRIEF DESCRIPTION OF THE DRAWINGS

FIG. 2 is a perspective, partial cross-sectional view of a reservoir-based drug delivery device having reservoir caps that open by electrothermal ablation, wherein the reservoirs can be loaded with a drug formulation and release-modifying agent as described herein.

DETAILED DESCRIPTION OF THE INVENTION

Figure 1A:
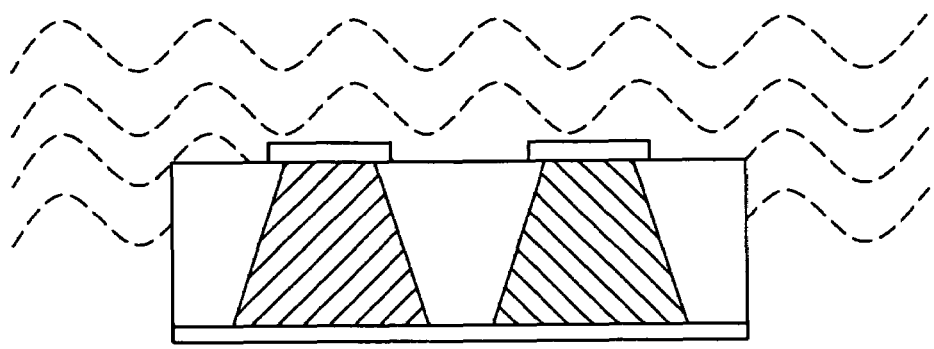
FIGS. 1A-C are cross-sectional views showing the operation of one embodiment of a drug delivery device comprising a drug formulation stored in a first reservoir and a release-modifying agent disposed in an adjacent second reservoir.

Formulations and methods have been developed to control the release of dosages of drugs from a reservoir-based drug delivery device by altering the local environment (also called "microenvironment") in or adjacent to the device, or by altering the chemical or physical properties of the drug formulation, with release-modifying agents that are stored in (the same or other) reservoirs in the device. This advantageously enables drug formulations to be stored and delivered from tiny spaces or through narrow openings (e.g., microreservoirs) where certain drug formulations might otherwise tend to precipitate, gel, or aggregate upon exposure to the physiological fluid into which the drug is to be delivered. This may enable more flexibility in tailoring other performance characteristics of the drug formulations, such as enhancing storage stability and/or reducing storage volume in the delivery device. For instance, the present formulations and methods advantageously may permit protein drug formulations to be stored and delivered in concentrated, rather than dilute, forms.

For instance, one of the challenges with certain drugs, e.g., certain proteins or other macromolecules, is that its solubility at physiological pH is limited, and that as the formulation within the reservoir contacts physiological fluid there is the potential for a precipitate or gel to form, adversely affecting the drug's release. However, once the drug molecules leave the device, they experience what one might think of as "infinite dilution" conditions, where solubility limits are of lesser concern. In another instance, the biological activity of some therapeutic molecules is dependent on achieving pulsatile delivery of sufficiently narrow pulse width. The inclusion of a release modifying agent can decrease or otherwise control the pulse width. The present approaches have been devised for managing the pH in the region of concern, i.e., the microenvironment in and adjacent to the drug containing reservoir and release opening. For instance, if the maximum solubility of the drug in aqueous solution occurs at solution pHs that are less than physiological pH (i.e., acidic environments), then the present methods enable one to maintain a low pH in the reservoir during the drug release event. The present methods, formulations, and devices may be critical to obtaining the necessary in vivo release kinetics for certain drug molecules or drug formulations.

As used herein, the term "release-modifying agent" (referred to herein occasionally as "transient modifiers") means a formulation excipient that promotes the dissolution, solubility, and/or physical stability of a drug. The release-modifying agent preferably is non-volatile, especially if it is introduced into the device or formulation prior to a lyophilization or other low pressure process step. For hPTH(1-34), the release-modifying agent preferably is an organic acids, and preferably is solid at 37° C. The release-modifying agents may be released to the local environment or added to the drug formulation to enhance the release of the drug or increase the delivery rate of the drug. In preferred embodiments, the release of a highly concentrated drug is enhanced by a release-modifying agent that inhibits or prevents gelation, aggregation, or precipitation of the drug in the reservoir or upon release to the microenvironment.

As used herein, the "local environment" refers to the environment external and proximate to the device reservoir(s) and the environment within the reservoir(s) containing the drug to be released including biological fluids and tissues at a site of implantation, air, fluids, and particulates present during storage or in vitro use of the drug delivery device.

As used herein, the terms "comprise," "comprising," "include," and "including" are intended to be open, non-limiting terms, unless the contrary is expressly indicated.

The present methods may be useful in conjunction with a wide variety of drug formulations and drug delivery devices. In a preferred embodiment, an implantable medical device is provided for the storage and controlled release of a drug formulation in vivo. In a general embodiment, the device comprises: a body portion; at least one reservoir located in at least one surface of the body portion and having at least one release opening; at least one drug formulation, which comprises at least one drug, disposed within the at least one reservoir; and a release-modifying agent disposed within the at least one of the reservoirs or within one or more second reservoirs. In one embodiment, the device may further include at least one reservoir cap closing off the release opening; and activation means for selectively disintegrating the reservoir cap to permit release of the drug formulation from the at least one reservoir. Preferably, the activation means for selectively disintegrating the reservoir cap comprises electrical circuits, a power source, and a controller for disintegrating the reservoir caps by electrothermal ablation.

The release-modifying agents may be stored in the same reservoir as the drug or in a nearby reservoir depending upon capability, capacity, desired effect, and the desired volume of effect. Release of the drug and release-modifying agent are coordinated so that the transient modification of the local microenvironment is properly timed to effect the enhancement of release of the drug. In particular embodiments, the release-modifying agents are designed to be released in the vicinity (i.e., in the local microenvironment) into which the drug is to be released. The release-modifying agent may be in the same reservoir as the drug formulation, as (1) a part of a mixture or other integral part of the drug formulation, (2) separate one or more layers of drug formulation and one or more layers of release-modifying agent, or (3) a combination thereof.

If the release-modifying agent is released from reservoirs other than the reservoir that actually contains the drug, then it typically will be one or more reservoirs near the opened drug-containing reservoir. In addition, reservoir cap disintegration of both types of reservoirs (i.e., drug containing or release-modifying agent containing) typically would be synchronized or timed to be at the same time, immediately before or immediately after one another. For example, this timing or synchronization can be controlled by a microprocessor in the device itself or wirelessly by remote means, which are discussed in further detail below.

Figure 1B:
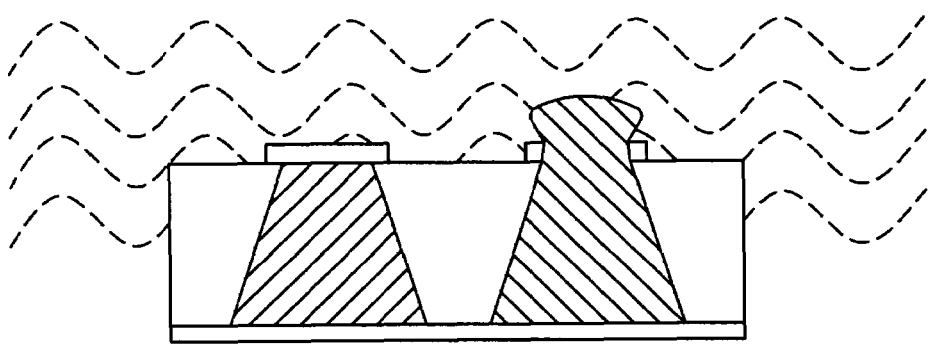
Figure 1C:
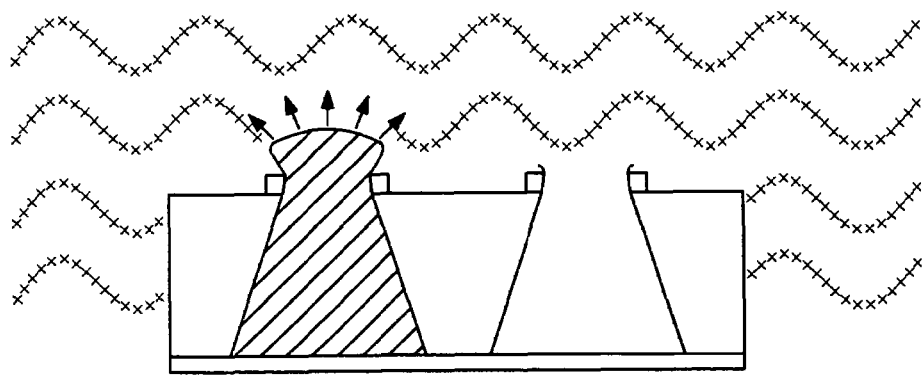

FIG. 1A illustrates one embodiment of a drug delivery device comprising a drug formulation stored in a first reservoir and a release-modifying agent disposed in a nearby second reservoir. Both reservoirs are covered with discrete reservoir caps. In addition, the drug delivery device is disposed in a physiological local environment. FIG. 1B illustrates the removal of the reservoir cap covering the second reservoir and the release of the release-modifying agent into the local environment. Once the release-modifying agent is released into the local environment it creates a modified local environment. FIG. 1C illustrates the removal of the reservoir cap covering the first reservoir and the release of the drug formulation into the modified local environment, with an enhanced delivery rate.

In one particular embodiment, the drug delivery device incorporating these formulations and methods comprises (i) a body portion (ii) a plurality of discrete reservoirs located in the body portion (iii) a drug disposed within a least one of the reservoirs and (iv) a release-modifying agent disposed within at least one of the reservoirs. The reservoirs can be individually filled and addressed, enabling the time and rate of release of multiple contents to be controlled. In addition, the reservoirs can be closed by reservoir caps. In a preferred embodiment, a discrete reservoir cap completely covers a single reservoir opening. In another embodiment, a discrete reservoir cap covers two or more, but less than all, of the reservoir's openings, as described in U.S. patent application Ser. No. 11/217,799, filed Sep. 1, 2005, which is incorporate herein by reference. The device further includes active or passive means to selectively disintegrate or rupture each reservoir cap to initiate release of the drug formulation from the device. The devices can further include a packaging structure to protect the electronic systems (which control the release mechanisms) of the device from the environment, especially for implantation for use in in vivo applications.

In one embodiment, each reservoir of the device has at least two openings with a support structure therebetween. The release openings typically are adjacent to one another, e.g., in an array, wherein the reservoir openings are covered by discrete reservoir caps. These multiple openings can effectively and advantageously act like a single larger opening (from a mass transport perspective), yet permit the effective opening size to be covered by a selectively removable/openable structure that is self-supporting across the opening.

The support structure, a reservoir cap support, is disposed under the reservoir caps, in or over the reservoir, to support the reservoir caps in part. The openings of the reservoir are defined, in part, by a support structure disposed under and supporting the outer edge part of the reservoir caps. The support structure may be located outside of the reservoir or located both inside and outside of the reservoir.

The reservoir cap supports can comprise substrate material, structural material, or coating material, or combinations thereof. Reservoir cap supports comprising substrate material may be formed in the same step as the reservoirs. microfabrication, micromolding, and micromachining techniques may be used to fabricate the substrate/reservoirs, as well as reservoir cap supports, from a variety of substrate materials. Reservoir cap supports comprising structural material may also be formed by deposition techniques onto the substrate and then MEMS methods, microfabrication, micromolding, and micromachining techniques. Reservoir cap supports formed from coating material may be formed using known coating processes and tape masking, shadow masking, selective laser removal techniques, or other selective methods. The dimensions and geometry of the support structure can be varied depending upon the particular requirements of a specific application. For instance, the thickness, width, and cross-sectional shape (e.g., square, rectangular, triangular) of the support structures may be tailored for particular drug release kinetics for a certain drug formulation or implantation site.

Figure 6:
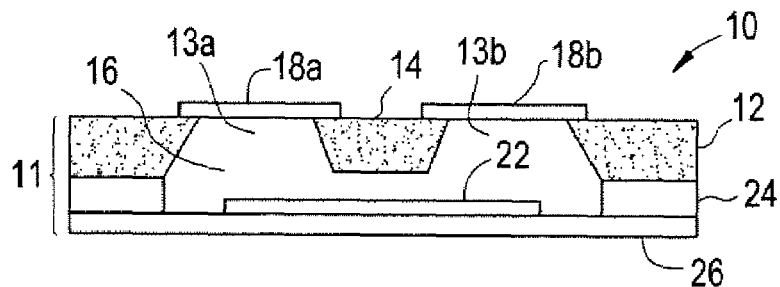
FIG. 6 is a cross-sectional view of one embodiment of a multi-cap reservoir device.

FIG. 6 is a cross-sectional view of one embodiment of a multi-cap reservoir device. The device 10 includes a substrate 11, which comprises a first substrate portion 12, a second substrate portion (i.e., spacer) 24, and a sealing layer 26. The three components 12, 24, and 26 are bonded together and define reservoir 16. Part of the first substrate portion serves as reservoir cap support 14 and spans the reservoir 16 (into and out of the drawing sheet in FIG. 6). The reservoir 16 has a plurality (two are shown) of openings 13a and 13b, sealed closed by reservoir caps 18a and 18b, respectively. These reservoir caps are in part supported by reservoir cap support 14 and cover the reservoir 16 to isolate secondary device 22 located therein. The secondary device 22 is secured to sealing layer 26. It is noted that in another embodiment, a separate sealing layer is not required where the bottom surface of the reservoir is integrally formed with the sidewalls, e.g., where the second substrate portion and sealing layer are unitary.

Figure 7A:
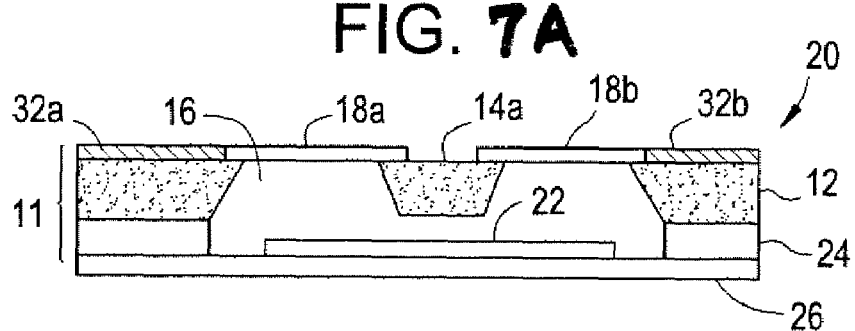
FIGS. 7A-B show a cross-sectional view (FIG. 7A) and a plan view (FIG. 7B) of one embodiment of a multi-cap reservoir device that includes reservoir caps formed of a conductive material and in electrical connection with a pair of leads for passing an electrical current effective to disintegrate the reservoir caps by electrothermal ablation.
Figure 7B:
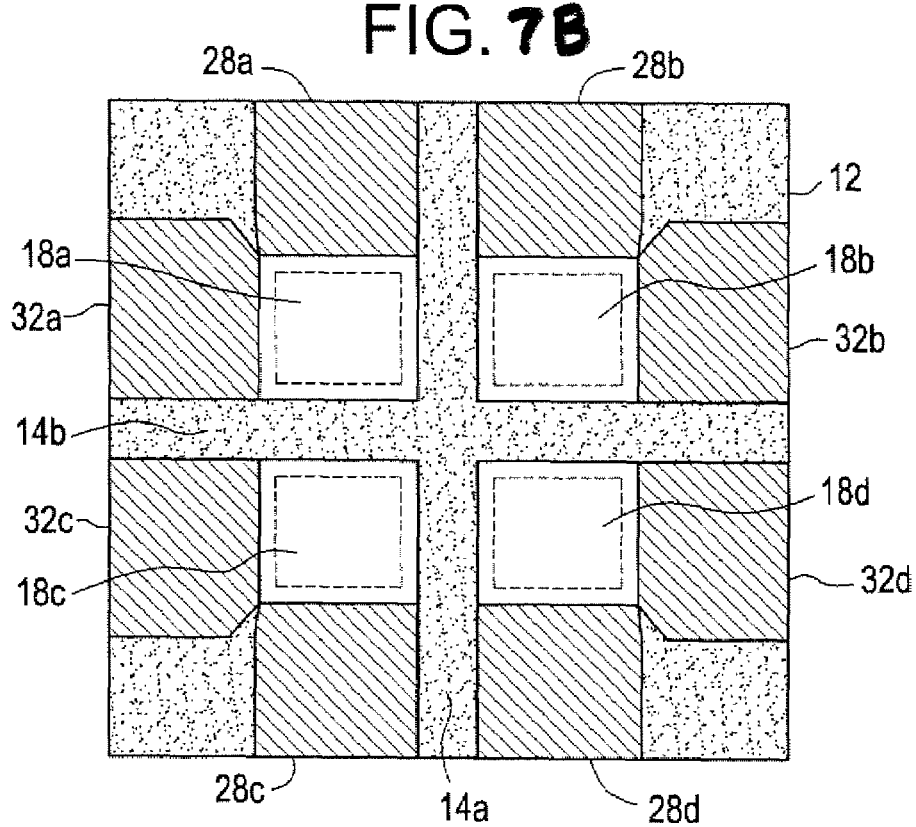

In one particular embodiment the reservoir caps are formed of a conductive material and in electrical connection with a pair of leads for passing an electrical current effective to disintegrate the reservoir caps by electrothermal ablation, as described in U.S. Patent Application Publication No. 2004/0121486 A1 to Uhland et al. FIGS. 7A-B show a cross-sectional view (FIG. 7A) and a plan view (FIG. 7B) of such an embodiment. The device 20 includes a substrate 11, which comprises a first substrate portion 12, a second substrate portion (i.e., spacer) 24, and a sealing layer 26. The three components 12, 24, and 26 are bonded together and define reservoir 16. Part of the first substrate portion 12 serves as reservoir cap support 14 and spans the reservoir 16. The reservoir 16 has a plurality (four are shown in FIG. 7B) of openings sealed closed by reservoir caps 18a, 18b, 18c, and 18d. The reservoir caps are in part supported by reservoir cap supports 14a and 14b and cover the reservoir 16 to isolate secondary device 22 located therein. The secondary device 22 is secured to sealing layer 26. On the surface of substrate portion 12, reservoir caps 18a, 18b, 18c, and 18d are electrically connected, respectively, to input lead and output lead pairs 28a/32a, 28b/32b, 28c/32c, and 28d/32d. The leads are connected to a source of electric power (not shown) for applying an electrical current through each of the reservoir caps. Upon application of an electrical current through the reservoir caps, via the input leads and output leads, the reservoir caps are disintegrated to release the drug and/or release modifying agent. In one embodiment, the source of electrical current is a capacitor that is charged locally by an on-board battery or remotely by an RF signal.

In operation, the reservoir caps 18a, 18b, 18c, and 18d are disintegrated, serially or simultaneously, by electrothermal ablation to open the reservoir and expose the secondary device to one or more environmental components outside the device. As can be understood from the foregoing description and FIGS. 7A-B, the four reservoir caps each cover roughly a quarter of the total area available for material to pass into and/or out of the reservoir. This opening system thus provides greater flexibility for controlling the transport rate and permits the use of larger reservoirs with larger effective openings with reservoir caps that have a construction and dimensions that could not be self-supporting. It also can provide reservoir cap(s) able to withstand stresses greater than its own weight, as well as normal or expected stresses incurred in the device's intended application.

Figure 8:
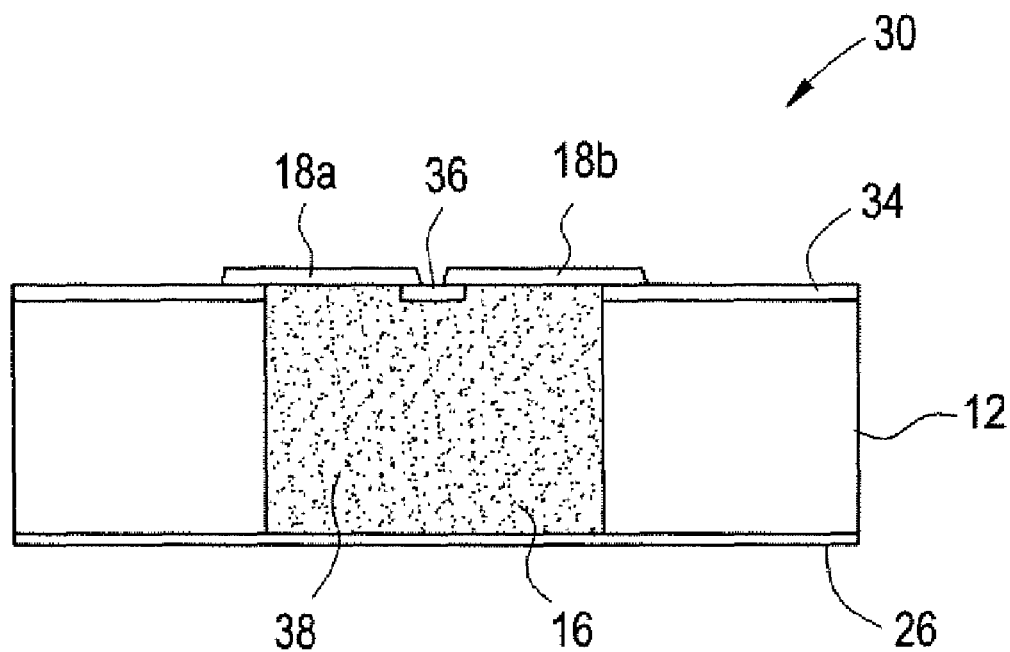
FIG. 8 is a cross-sectional view of one embodiment of a multi-cap reservoir device in which the reservoir cap support is made from a coating or deposited material that is distinct from the substrate or that is a very thin layer of a multilayer substrate.

In another embodiment, the reservoir cap support is made from a coating or deposited material that is distinct from the substrate, or that is a very thin layer of a multilayer substrate. FIG. 8 is a cross-sectional view of one such embodiment. The device 30 includes a substrate 12 and sealing layer 26, which together essentially define reservoir 16. The reservoir 16 has a plurality (two are shown) of openings, which are sealed closed by reservoir caps 18a and 18b. The reservoir caps are supported by coating layer 34, which includes reservoir cap support 36. A drug formulation 38 is loaded in and isolated inside reservoir 16 until the reservoir caps are actuated (e.g., disintegrated).

In FIG. 6, the support structure is a portion of the substrate or is fabricated out of (a portion of) the substrate. In such a case, the material of the substrate and the support structure are the same and integrally connected/formed, because at one point in the fabrication process the support structure and the substrate were indistinguishable. By contrast, in FIG. 8, the support structure and the substrate are different, either in the sense that they have different composition (i.e., are formed from different materials) or in the sense that they have the same composition but are created in distinct steps/different methods. For instance, a silicon substrate could be grown from a single crystal and a silicon support structure could be deposited using various deposition methods. The support material can be deposited using a range of methods known in the art, including microfabrication/micromachining methods such as plasma sputtering, e-beam evaporation, ion-beam sputtering or evaporation, various chemical vapor deposition (low pressure or plasma-enhanced) methods, and spin coating (spin-on glass or various polymers). Such support layers also could be grown thermally, such as the growth of a thick silicon oxide layer on silicon. In any of these methods, the "deposited" layer is patterned in some way to create the support structure.

For clarity, only one reservoir is shown in FIG. 6; however, the device can include an array of several reservoirs, each of which has its own multiple reservoir caps. It should also be noted for clarity that the reservoir is a sealed enclosure despite any appearance to the contrary suggested by the "cut-away" cross-section view of FIGS. 6, 7A, and 8.

Further details about the reservoirs, reservoir caps, drugs, reservoir opening technologies (e.g., power source and control circuitry for selective disintegration of reservoir caps) and other features of preferred reservoir-based drug delivery devices are described below and, for example, in U.S. Pat. No. 5,797,898, U.S. Pat. No. 6,527,762, U.S. Pat. No. 6,491,666, U.S. Pat. No. 6,551,838, U.S. Pat. No. 6,773,429, and U.S. Pat. No. 6,827,250, which are incorporated by reference herein. In a preferred embodiment, the devices employ electrothermal ablation to open the reservoirs, as taught in U.S. Patent Application Publication No. 2004/0121486 A1 to Uhland et al., which is incorporated by reference herein.

Reservoir Contents

In one embodiment, the reservoirs contain molecules which need to be stored and then released into the surrounding environment. In addition, the reservoirs contain release-modifying agents which enhance the release of the stored molecules.

In other embodiments, the reservoirs of a device may contain a secondary device (e.g., a sensor), alone or in combination with a drug formulation for controlled release. Examples of useful sensors include biosensors (e.g., for the chemical detection of one or more analytes in a physiological fluid), pressure sensors, and pH sensors. In one embodiment, the biosensor comprises an enzyme or antibody. In one embodiment, the sensor measures glucose levels in vivo, which may include a glucose oxidase component, as described for example in U.S. Patent Application Publication No. 2005/0096587 A1, which is incorporated herein by reference. In one embodiment, sensors are provided in a first array of reservoirs, and a drug formulation is provided in a second array of reservoirs. In a preferred embodiment, the reservoir contents comprise a sensor or sensor component hermetically sealed in the reservoirs at a reduced pressure and/or with an inert gas.

Drugs and Other Agents of Interest for Release

The reservoir contents can include essentially any natural or synthetic, organic or inorganic molecule or mixture thereof, for release (i.e., delivery). The molecules (i.e., chemicals) may be in solid, liquid, or gel form. Chemicals may be in the form of solid mixtures, which may include amorphous and crystalline mixed powders, monolithic solid mixtures, lyophilized powders, and solid interpenetrating networks; in the form of liquid mixtures which may include solutions, emulsions, colloidal suspensions, and slurries; and in the form of gel mixtures which may include hydrogels.

For in vivo applications, the chemical preferably is a therapeutic, prophylactic, or diagnostic agent. In one embodiment, the microchip device is used to deliver drugs systemically to a patient in need thereof. In another embodiment, the construction and placement of the microchip in a patient enables the local or regional release of drugs that may be too potent for systemic delivery of an effective dose. As used herein, "drugs" include any therapeutic, prophylactic or diagnostic agent, including organic or inorganic molecules, proteins, nucleic acids, polysaccharides and synthetic organic molecules, having a bioactive effect. The drugs can be in the form of a single drug or drug mixtures and can include pharmaceutically acceptable carriers.

The drugs are desirably provided in a solid form, particularly for purposes of maintaining or extending the stability of the drug over a commercially and medically useful time, e.g., during storage in a drug delivery device until the drug needs to be administered. The solid drug matrix may be in pure form or in the form of solid particles of another material in which the drug is contained or dispersed. As used herein, "pure form" of the drug includes the active pharmaceutical ingredient (API), residual moisture, and any chemical species combined with the API in a specific molar ratio that is isolated with the API during preparation of the API (for instance, a counter-ion) and which has not been added as an excipient. In its dry solid matrix form, the drug may be a free-flowing powder, an agglomerated "cake," or some combination thereof. The terms "dry solid" include powders, crystals, microparticles, amorphous and crystalline mixed powders, monolithic solid mixtures, and the like. The terms "pre-form" and "pellet" refers to a small, solid form of the drug matrix loaded with the solidified excipient material.

In a preferred embodiment, the drug is stored and released in a concentrated form such as concentrated lyophilized dosages and concentrated organic solvent solutions, for example. In other embodiments, the drug formulation can be in a molten solution or suspension.

The drug can comprise small molecules, large (i.e., macro-) molecules, or a combination thereof. In one embodiment, the large molecule drug is a protein or a peptide. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics, immunosuppressants, analgesic agents, and vitamins. In a preferred embodiment, the drug is a protein. Examples of suitable types of proteins include, glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., alpha-, beta-, or gamma-interferons), interleukins (e.g., IL-2, IL-10), and diabetes/obesity-related therapeutics (e.g., insulin, PYY, GLP-1 and its analogs). In one embodiment, the drug is a gonadotropin-releasing (LH-RH) hormone analog, such as leuprolide.

In one particular embodiment, the drug comprises parathyroid hormone. It may be the naturally occurring form of parathyroid hormone in humans (hPTH(1-84)), or it may be a natural or synthetic analog thereof. For instance, the drug formulation may consist of or include teriparatide (e.g., FORTEO™). Various embodiments of such drug formulation-device combinations are described in U.S. Patent Application Publication No. 2004/0082937, which is incorporated herein by reference.

In one embodiment, the drug formulation comprises an incretin mimetic, such as an exenatide (e.g., BYETTA™).

In another embodiment, the drug formulation comprises an antihyperglycemic agent, such as a synthetic amylin analog (e.g., SYMLIN™)

In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP).

In one embodiment, the reservoir contents of the devices described herein may include a peptide or protein having therapeutic potential. This may be selected from among antibodies, nucleosides, nucleotides, oligonucleotides, and analogs thereof.

In another embodiment, the reservoir contents of the devices described herein may include at least one RNA-, iRNA-, or DNA-based diagnostic or therapeutic agent.

Release-Modifying Agents

The release-modifying agent can be essentially any biocompatible compound or mixture that functions to inhibit gelation or aggregation of the drug, drug formulation, or a component thereof, when the drug, drug formulation, or a component thereof comes into contact with a physiological fluid in the environment inside or immediately outside of the drug reservoir. In a preferred embodiment, the release-modifying agent functions by adjusting the pH of the fluid microenvironment within and/or adjacent the drug-containing reservoir. In other embodiments, the hydrophobic/hydrophilic nature of the local environment may be altered through the use of co-solvents, viscosity modifiers (e.g., saccharides), or chaotropic agents (e.g., urea).

The release-modifying agent can, for example, be a buffering agent, such as an acid or a base. For example, simple bases and polymeric acidic and/or alkaline forms, such as carboxylated polysaccharides or other polyanionic/polyacidic modifiers, may be used as release-modifying agents. Representative examples of other release-modifying agents include citric acid, acetic acid, succinic acid, fumaric acid, pivalic acid, lactic acid, tartaric acid, amino acids, other water-soluble organic acids, and their conjugate bases. Citric acid may be preferred.

In addition to promoting complete dissolution at physiological pH, the release-modifying agent may promote fast dissolution and release. This can aid control of a narrow pulse width in a pulsatile delivery system.

In preferred embodiments, non-volatile, monoprotic or polyprotic organic acids can be used as a release-modifying agent. One of the desirable properties of these release-modifying agents is that when they are added to drug formulations that are later lyophilized, they will remain in the drug formulation after the lyophilization process. Examples of suitable non-volatile, polyprotic, organic acids include citric acid and tartaric acid.

In other embodiments, the release-modifying agents can be in the form of polymers, salts, including polymeric salts, and surfactants, including ionic and non-ionic surfactants. Additional examples of release-modifying polymers, include, but are not limited to, neutral, ionic, and either poly-acidic or poly-basic forms.

In another aspect, the release-modifying agent is an excipient that function (i.e., inhibit gelation/aggregation/precipitation) by providing a "more desirable" cake structure to lyophilized dosage forms. For example, by producing a particular "pore size" one may control the rate of solvent absorption that occurs via capillary action. Pore size will be determined by a number of factors, which can include the excipient identity and concentration. In addition, the excipient morphology (i.e., crystalline or amorphous) will have an influence on the dissolution rate of the lyophilized form. These mechanisms may contribute to the increased rate(s) of dissolution noted above when including the "transient modifier" in the reservoir's primary fill.

An appropriate excipient may also inhibit non-pH dependent mechanisms of self-association. For example, if the gelation/aggregation/precipitation occurs through the intermolecular or intramolecular association of hydrophobic domains, then a particular excipient with some hydrophobic character (e.g., a surfactant) may be able to preferentially bind to the hydrophobic domains of the molecule, thereby inhibiting the intermolecular and/or intramolecular associations that can cause gelation/aggregation/precipitation.

Examples of release-modifying agents include agents that inhibit or prevent gelation/aggregation/precipitation events. These could be in the form of polymers, salts—including polymeric salts, and surfactants—including ionic and non-ionic surfactants. The release-modifying agents that have been tested with PTH in various experiments (see Examples below) have been relatively simple mono- and polyprotic organic acids. Non-volatile acids have been considered because they will remain in the reservoir with the drug formulation after a lyophilization process.

Excipients

In embodiments where the drug formulation is a porous solid, the void-volume in the solid may be desirably filled with excipients. The excipients may comprise a solid, a liquid, or a solid formed from a liquid, for example. Examples of suitable excipients include, but are not limited to, polymers such as polyethylene glycol. In some embodiments, more than one excipient may be added to one reservoir having a porous solid drug formulation.

In one embodiment, the drug formulation is in a lyophilized form and the release-modifying agent is mixed with an excipient material (e.g., polyethylene glycol), where the excipient mixture is loaded in fluid form into/onto the lyophilized material disposed in the reservoir to fill the reservoir (e.g., to eliminate gas spaces in the reservoir) and then is subsequently solidified. U.S. Patent Application Publication No. 2004/0247671 to Prescott et al., which is incorporated herein by reference, describes compositions and methods for adding excipient mixtures to reservoirs to facilitate release of drug formulations therefrom. The present improvement can be readily adapted to the devices of Prescott et al. to further enhance drug release control.

Release-Modifying Mechanisms and Devices

There are several approaches available for enhancing the release of drugs or drug formulations. One release-modifying technique is modification of the local environment pH. For example, in particular embodiments, the drugs or drug formulations to be released have limited solubility or undergo gelation, aggregation, or precipitation at physiological pH. Gelation, aggregation, or precipitation of these drugs or drug formulations can be prevented by changing the pH of the microenvironment into which the drugs or drug formulations are released. For instance, if a 100 nL drug dosage contains the equivalent of a 1M acid source, the acid would lower the pH of up to 10 microliters of physiological fluid (i.e., assuming a 10 mM buffering agent) once the drug formulation is exposed to the local environment. This lowering of the physiological fluid pH could allow a 100-fold dilution of the concentrated dosage before it encounters an unmodified physiological environment. Examples of suitable release-modifying agents for changing the pH of the local environment include acids, bases, and buffers for example.

In one embodiment, lowering of the physiological fluid pH can be used to enhance the release of drug formulations comprising teriparatide. Both concentrated lyophilized dosages and organic solvent solutions of teriparatide can form gels at physiological pH. However, by the inclusion of an acidic release-modifying agent in the reservoir containing teriparatide or in a nearby reservoir, the pH proximate (including within) the reservoir opening can be lowered. Examples of suitable release-modifying agents for these embodiments include, but are not limited to, tartaric acid and citric acid.

Another method of enhancing the release of drug formulations comprising teriparatide involves keeping the teriparatide in solution. Since the maximum solubility of teriparatide in an aqueous solution occurs at a pH less than physiological pH (i.e., an acidic environment), keeping the drug formulation acidic keeps the teriparatide in solution. Thus, adding a release-modifying agent to the reservoir containing the teriparatide to keeps the teriparatide in solution. The teriparatide solution can then be released from the reservoir more quickly than a teriparatide solution without the release-modifying agent. Once released, the teriparatide solution disperses and experiences "infinite dilution" conditions (i.e., where solubility limits are higher and do not affect release of the teriparatide) more quickly. Examples of suitable acids for use in these embodiments include, but are not limited to, tartaric acid and citric acid.

A second embodiment uses a release-modifying agent to either create pores or change the pore size of a solid drug formulation in a reservoir to cause or enhance the flow of a fluid into the reservoir from the microenvironment.

In some embodiments, a pressure gradient can be created and used to cause a physiological fluid to flow into a reservoir containing a drug formulation by preparing a drug formulation (with or without a release-modifying agent) to create a solid with void-volume. The reservoir can then be covered and sealed with the reservoir cap under reduced pressure (i.e., vacuum or partial vacuum). When the reservoir cap is removed, the physiological fluid is drawn into the reservoir by the pressure gradient created when the reservoir cap was removed. In this manner, the drug formulation release is enhanced because dissolution of the drug formulation into the physiological environment is accelerated. A void-volume displacer would not be required and would in fact hinder dissolution of the drug formulation during its release. Thus, void-volume displacing excipients may not be required or desired if the porous drug form, possibly including a release-modifying agent, is sealed under reduced pressure.

In other embodiments, the rate of fluid flow into the reservoir having the drug formulation can be accelerated by altering the pore size of a solid drug formulation. For example, the cake structure of a lyophilized drug formulation can be altered by a release-modifying agent which causes the lyophilized drug formulation to have a particular pore size which maximizes the capillary action through the solid. Thus, the addition of a release-modifying agent to the drug formulation can allow for control of the rate of solvent absorption that occurs via capillary action through the drug formulation cake. Again, the faster the physiological fluid enters the reservoir, the faster the dissolution rate of the drug formulation. It should be understood that the pore size is dependant upon a number of factors, including the release-modifying agent concentration and morphology (i.e., whether it is crystalline or amorphous).

A third embodiment uses a release-modifying agent which either bonds to hydrophilic and/or hydrophobic domains of the drug or drug formulation to prevent intermolecular or intramolecular associations. In embodiments where gelation, aggregation, or precipitation occurs through the intermolecular or intramolecular association of hydrophilic and/or hydrophobic domains on the drug formulation molecules, a release-modifying agent could be introduced to prevent these associations. For example, a release-modifying agent can be introduced to preferentially bind to the hydrophobic domains of the drug formulation molecules. Since the release-modifying agent is bound to the hydrophobic domains, hydrophobic interactions between the drug formulation and the physiological environment cannot occur and the release of the drug is enhanced. Examples of suitable release-modifying agents to prevent hydrophilic and/or hydrophobic associations include, but are not limited to, surfactants and polymers.

In other embodiments, the hydrophobic/hydrophilic nature of the local environment may be altered through the use of co-solvents, viscosity modifiers such as saccharides, or chaotropic agents such as urea. Thus, hydrophobic and/or hydrophilic associations between the local environment and the drug formulations can be avoided and the release of the drug formulation is enhanced.

Various other embodiments use a release-modifying agent to change either the phase or morphology of the drugs or drug formulations. For example, a release-modifying agent may be added to a drug formulation to create either a crystalline or amorphous solid which would dissociate quickly in a physiological environment.

In yet other embodiments, the release-modifying agent prevents reactions of the drug or drug formulation with the physiological environment. For example, a release-modifying agent could be included in a drug delivery device to inhibit oxidation of the drug formulation with the physiological environment.

Additional Device Details

The drug delivery device includes a body portion comprising reservoirs having reservoir contents such as a drug formulation (with or without a release-modifying agent), and a means for actively opening the reservoirs to control release or exposure of the reservoir contents. The structure of the device, or at least the reservoir portion thereof, may be further understood by reference to FIG. 2.

Body Portion and Reservoirs

The body portion contains the reservoirs and serves as the support for the drug delivery device. Any material which can serve as a support, which is suitable for etching or machining or which can be cast or molded, and which is impermeable (during the time scale of the microchip's use) to the contents of the reservoir and to the surrounding environment may be used as a body portion. Suitable materials include metals, semiconductors, polymers, and ceramic materials. An example of a suitable semiconductor material includes silicon. Representative examples of ceramic materials include alumina (aluminum oxide), aluminum nitride, silicon dioxide, silicon nitride, and other various nitrides and oxides. The body portion can be formed of only one material or can be a composite or multi-laminate material. In addition, the body portion may comprise a chip, a disk, a tube, or a sphere, for example.

For in vivo applications, the body portion generally is formed of or coated with a biocompatible material. Non-biocompatible materials may be encapsulated or contained in a biocompatible material, such as parylene, poly(ethylene glycol), polytetrafluoroethylene-like materials, or titanium, before use. For in vitro applications, such as in medical diagnostics, the body portion can be constructed of biocompatible or non-biocompatible materials.

In one embodiment, the reservoirs are microreservoirs. A "microreservoir" is a reservoir having a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.). In another embodiment, the reservoirs are macroreservoirs. A "macroreservoir" is a reservoir having a volume greater than 500 µL (e.g., greater than 600 µL, greater than 750 µL, greater than 900 µL, greater than 1 mL, etc.) and less than 5 mL (e.g., less than 4 mL, less than 3 mL, less than 2 mL, less than 1 mL, etc.). In a particular embodiment, the volume is between 500 nL and 10 µL. The shape and dimensions of the reservoir, as well as the number of reservoirs, can be selected to control the contact area between the drug material and the surrounding surface of the reservoirs. Unless explicitly indicated to be limited to either micro- or macro-scale volumes/quantities, the term "reservoir" is intended to encompass both.

Reservoir Caps and Means for Disintegrating/Opening Reservoir Caps

As used herein, the term "reservoir cap" includes a membrane or other structure suitable for separating the contents of a reservoir from the environment outside of the reservoir. It generally is self-supporting across the reservoir opening, although supports could be built into the cap. Selectively removing the reservoir cap or making it permeable will then "expose" the contents of the reservoir to the environment (or selected components thereof) surrounding the reservoir. In preferred embodiments, the reservoir cap can be selectively disintegrated, e.g., on demand. As used herein, the terms "disintegrate," "disintegration," and "disintegrating" in reference to reservoir caps include any mechanism of loss of structural integrity and thus loss of barrier to the environment outside of the reservoir, including oxidation, mechanical rupture, degradation or dissolving, unless otherwise indicated. The "mechanical rupture" typically does not include puncturing the reservoir cap from the outside, such as with a needle. In one embodiment, the reservoir cap is composed of a metal, such as copper, gold, and silver, which is disintegrated by electrochemical dissolution via the application of electrical potential, as described in U.S. Pat. No. 5,797,898 to Santini.

In active devices, the reservoir cap includes any material that can be disintegrated or permeabilized in response to an applied stimulus (e.g., electric field or current, magnetic field, change in pH, or by thermal, chemical, electrochemical, or mechanical means). In one embodiment, the reservoir cap is a thin metal membrane and is impermeable to the surrounding environment (e.g., body fluids or another chloride containing solution). Based on the type of metal and the surrounding environment, a particular electric potential is applied to the metal reservoir cap, which is then oxidized and disintegrated by an electrochemical reaction, to expose the contents of the reservoir to the surrounding environment. Examples of suitable reservoir cap materials include gold, silver, copper, and zinc. Any combination of passive or active barrier layers can be present in a single microchip device.

Means for Controlling Release

Means for controllably releasing the molecules from active devices require actuation, which typically is done under the control of a microprocessor. For example, in one embodiment, the drug delivery device includes a body portion having a two-dimensional array of reservoirs arranged therein, a release system comprising drug molecules contained in the reservoirs, anode reservoir caps covering each of the reservoirs, cathodes positioned on the body portion near the anodes, and means for actively controlling disintegration of the reservoir caps. Preferably, such means includes an input source, a microprocessor, a timer, a demultiplexer, and a power source. The power source provides energy to drive the reaction between selected anodes and cathodes. Upon application of a small potential between the electrodes, electrons pass from the anode to the cathode through the external circuit causing the anode material to oxidize and dissolve into the surrounding fluids, exposing the drug formulation for delivery to the surrounding fluids, e.g., in vivo. The microprocessor directs power to specific electrode pairs through a demultiplexer as directed, for example, by a PROM, remote control, or biosensor.

The microprocessor is programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor. Additionally, the disintegration or permeabilization of reservoir caps covering drug formulations may be timed to be in sequence with or at the same time as disintegration or permeabilization of reservoir caps covering release-modifying agents.

The criteria for selection of a microprocessor are small size, low power requirement, and the ability to translate the output from memory sources, signal receivers, or biosensors into an address for the direction of power through the demultiplexer to a specific reservoir on the drug delivery device (see, e.g., Ji, et al., *IEEE J. Solid-State Circuits* 27:433-43 (1992)). Selection of a source of input to the microprocessor such as memory sources, signal receivers, or biosensors depends on the drug delivery device's particular application and whether device operation is preprogrammed, controlled by remote means, or controlled by feedback from its environment (i.e. biofeedback).

The criteria for selection of a power source are small size, sufficient power capacity, the ability to be integrated with the control circuitry, the ability to be recharged, and the length of time before recharging is necessary. Batteries can be separately manufactured (i.e. off-the-shelf) or can be integrated with the microchip itself. Several lithium-based, rechargeable microbatteries are described in Jones & Akridge, *J. Power Sources,* 54:63-67 (1995); and Bates et al., *IEEE 35$^{th}$ International Power Sources Symposium, pp.* 337-39 (1992). These batteries are typically only ten microns thick and occupy 1 cm$^2$ of area. One or more of these batteries can be incorporated directly onto the drug delivery device. Binyamin, et al., *J. Electrochem. Soc.,* 147:2780-83 (2000) describes work directed toward development of biofuel cells, which if developed, may provide a low power source suitable for the operation of the present delivery devices and other microelectronic devices in vivo.

A microprocessor is used in conjunction with a source of memory such as programmable read only memory (PROM), a timer, a demultiplexer, and a power source such as a microbattery or a biofuel cell. A programmed sequence of events including the time a reservoir is to be opened and the location or address of the reservoir is stored into the PROM by the user. When the time for release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

The manufacture, size, and location of the power source, microprocessor, PROM, timer, demultiplexer, and other components are dependent upon the requirements of a particular application. In one embodiment, the memory, timer, microprocessor, and demultiplexer circuitry is integrated directly onto the surface of the drug delivery device. The microbattery is attached to the other side of the body portion and is connected to the device circuitry by vias or thin wires. However, in some cases, it is possible to use separate, prefabricated, component chips for memory, timing, processing, and demultiplexing. In one embodiment, these components are attached to the back side of the drug delivery device with the battery. In another embodiment, the component chips and battery are placed on the front of or next to the drug delivery device, for example similar to how it is done in multi-chip modules (MCMs) and hybrid circuit packages. The size and type of prefabricated chips used depends on the overall dimensions of the drug delivery device and the number of reservoirs, and the complexity of the control required for the application.

Methods of Making the Drug Delivery Devices

The basic drug delivery devices and components (i.e., reservoirs and reservoir caps) can be made using microfabrication methods known in the art, particularly those methods described in U.S. Pat. No. 5,797,898, U.S. Pat. No. 6,123,861, U.S. Pat. No. 6,808,522, U.S. Pat. No. 6,875,208, U.S. Pat. No. 6,527,762, U.S. Pat. No. 6,551,838, U.S. Pat. No. 6,976,982, U.S. Pat. No. 6,827,250, and U.S. Pat. No. 6,730,072, and in U.S. Patent application Publications No. 2004/0121486, No. 2004/0106914, and No. 2005/0096587, which are hereby incorporated by reference in their entirety.

Once reservoirs are formed into the body portion of the drug delivery devices, the molecules to be released and the release-modifying agents can be loaded into the reservoirs. In some embodiments, the drug formulation is loaded into one reservoir while the release-modifying agent is loaded into another, nearby reservoir. In other embodiments, the release-modifying agent is loaded into the same reservoir as the reservoir loaded with the drug formulation. For example, a release-modifying agent may be loaded in an initial loading step (also called the "primary fill") simultaneously with the drug formulation. Then, the reservoir contents may be further processed by, for instance, lyophilization. See, e.g., U.S. Patent Application Publication No. 2004/0043042, which is incorporated herein by reference. In embodiments where the drug formulation comprises a porous solid, a void-volume displacing agent, such as polyethylene glycol, may also be introduced into the porous drug cake. See, e.g., U.S. Patent Application Publication No. 2004/0247671, which is incorporated herein by reference.

In another embodiment, the drug formulation could comprise a porous solid, such as a lyophilized drug formulation and the release-modifying agent could be added after the drug formulation is solidified. In such an embodiment, the release-modifying agent could fill the pores in the solid. In addition, some embodiments may mix the release-modifying agent with an excipient material before filling the solid drug formulation voids with the mixture.

In alternate embodiments, layers of reservoir contents could be produced so that one or more layers of drug formulation are separated by and one or more layers of release-modifying agent and/or an excipient material.

In other embodiments, the release-modifying agent is added to the concentrated drug solution without lyophilization. For example, the drug formulation can be prepared in a molten solution or suspension containing the drug and the release-modifying agent. Alternatively, the drug formulation molten solution or suspension could comprise the drug, the release-modifying agent, and a void-volume displacing agent.

In still another embodiment, the drug formulation and/or the release-modifying agent is in the form of a pre-formed solid, shaped to fit into the reservoir. For example, the pre-forms may be pre-cast, e.g., made by a molding technique in a mold, and then transferred into the reservoirs using conventional pick and place techniques and equipment.

In one embodiment, the reservoirs of the device are filled in multiple steps. In one embodiment, the first step may be filling the reservoirs with a (concentrated) drug solution, freezing, and then lyophilizing the solution in the reservoir to yield a reservoir-bound porous drug form (e.g., a lyophilized cake), and then the second step may be introducing a void-volume displacing agent, such as a polyethylene glycol, into the cake. The release modifier may be introduced into the reservoir with the addition of the void-volume displacing agent, with the drug solution, or before or after these steps. In another embodiment, there is no freezing or lyophilization step.

In one example, a PTH solution is added to the reservoir, where citric acid is included as a non-volatile, polyprotic, organic acid modifier in the PTH solution. Tests have demonstrated on a "bulk" scale that the lyophilized cakes obtained from these solutions will dissolve quickly, and without mixing, in a mimetic of physiological fluid, wherein the "bulk" scale is typically 20 microliter (μL) aliquots of PTH solutions with PTH concentrations of 100 mg/mL or greater, which have been placed in glass vials and lyophilized. In addition to our "standard" supporting solution of 25% acetic acid in water, we also considered various combinations and concentrations of other organic acids in the solution. The resultant lyophilized cakes were considered on the basis of their physical appearance, the rate at which they dissolve when the mimetic of physiological fluid was placed on the cakes (no mixing), and on the basis of the measured recoveries of PTH following the apparent dissolution. In this way, it was demonstrated that the incorporation of the transient modifier in the primary fill would yield lyophilized forms, which dissolve more quickly and more completely than cakes obtained from solutions of PTH in 25% acetic acid without additional excipients. See the Examples below.

In another embodiment, the drug formulation is loaded into the reservoirs in one step, e.g., a primary fill alone. In one case, this primary fill may include a drug and a transient modifier, but not a void-volume displacing agent. If one were to seal the reservoirs under reduced pressure (e.g., vacuum), then, during use, physiological fluid could be "drawn into" the reservoir following reservoir cap disintegration. In this way, the void-volume displacer may not be needed, and if present might actually retard the dissolution and subsequent release of the drug formulation. In another case, the primary fill includes may include a drug, a transient modifier, and optionally a void-volume displacing agent. The formulation may be dispensed into the reservoirs as a molten solution or suspension, which could obviate the need to perform lyophilization. See, e.g., U.S. Patent Application Publication No. 2004/0247671, which is incorporated herein by reference.

Reservoir Sealing Under Reduced Pressure and/or With Inert Gas

Figure 3:
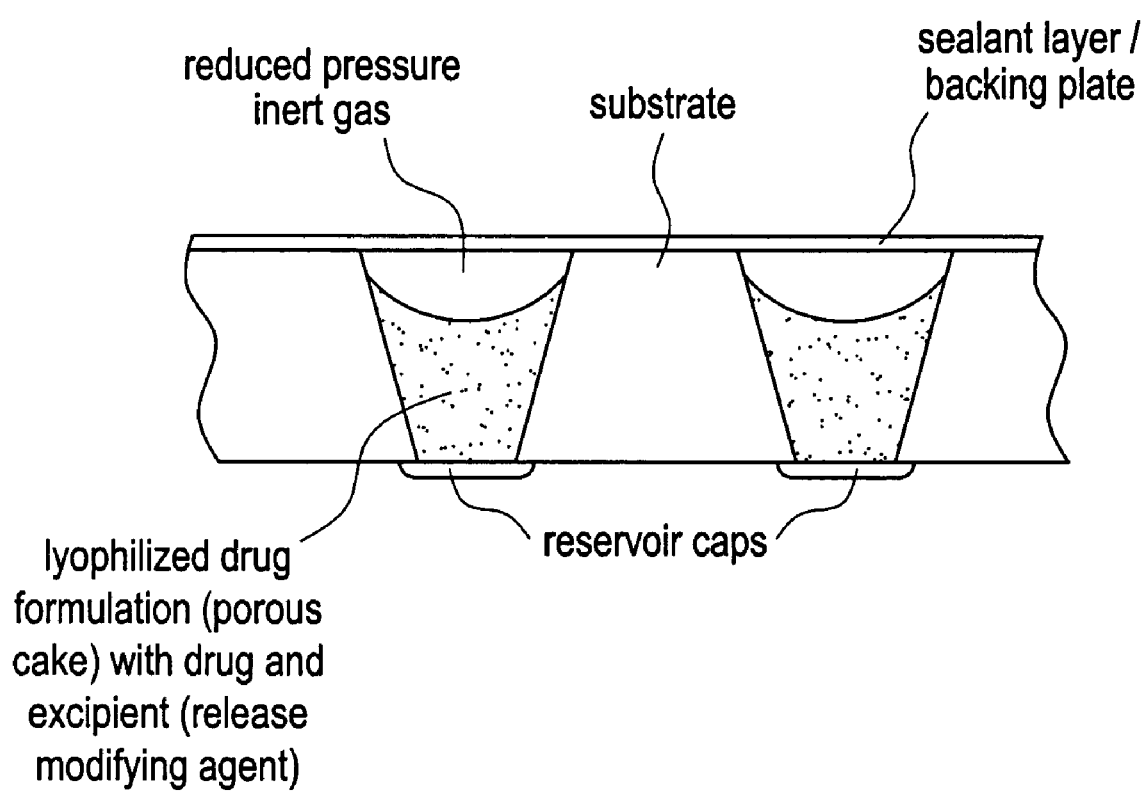
FIG. 3 is a cross-sectional view of a reservoir-based drug delivery device, wherein the reservoirs are sealed under reduced pressure with an inert gas.

In another highly advantageous aspect, devices and methods are provided for sealing and storing drug formulation dosage forms (or secondary devices, such as sensors) in reservoirs of a medical implant device under vacuum or reduced pressure conditions, and/or with an inert gas, to enhance the stability of the reservoir contents. See, e.g., FIG. 3. For one example, the reservoirs may loaded and sealed under vacuum conditions. As another example, the reservoirs may loaded and sealed in under a blanket of an inert gas. Representative examples of suitable inert gases include nitrogen ($N_2$), helium (He), argon (Ar), and combinations thereof. Methods and equipment needed to provide and maintain a reduced pressure and/or inert gas blanket environment during the reservoir filling and device assembly processes, are know in the art. Storing molecules (e.g., of the drug formulation or sensor) under a reduced pressure, particularly with an inert gas, advantageously should improve/extend molecular stability by slowing or preventing chemical degradation (e.g., by oxidation).

A further advantage of hermetically sealing the reservoirs under reduced pressure is that this may accelerate the release or exposure of reservoir contents, when the reservoir cap is removed/disintegrated. Specifically, the technique should promote the ingress of any fluids in contact with the reservoir cap at the time the reservoir cap is removed. This can increase the rate of dissolution of a solid drug formulation—without the need for a void-volume displacing fill (which fill otherwise may be necessary to avoid the presence of bubbles at the reservoir opening, bubbles that could block reservoir content egress or ingress). Similarly, this technique may be useful for shortening the response time of a sensor within a reservoir. This sealing of the reservoir can be done by a variety of techniques, including those described in U.S. Pat. No. 6,827,250, U.S. Patent Application Publication No. 2005/0050859, and U.S. application Ser. No. 11/267,541, filed Nov. 4, 2005, which are incorporated herein by reference.

The present invention is further illustrated by the following non-limiting examples.

The examples pertain to the release of hPTH(1-34). One of the challenges with PTH is that its solubility at physiological pH is limited, and that as the formulation within the reservoir contacts physiological fluid there is the potential for a precipitate or gel to form, adversely affecting the drug's release. Because the maximum solubility of PTH in aqueous solution occurs at solution pHs which are less than physiological pH (i.e. acidic environments), the examples describe ways to maintain a low pH in the reservoir during the release event. Once the drug molecules leave the reservoir, they experience what one might think of as "infinite dilution" conditions—where solubility limits are of lesser concern.

EXAMPLE 1

Enhanced Release of Teriparatide from Reservoir Using with Tartaric Acid/PEG Backfill A teriparatide solution was prepared adding 200 mg of teriparatide per milliliter of solution to a 25% acetic acid in water mixture. (The acid concentration is approximate, as it assumes no volumetric contribution of the teriparatide to the solution.) Device/substrate reservoirs were filled using 100-125 nL of the teriparatide solution. The teriparatide was then lyophilized to yield a solid dosage. For concentrated lyophilized dosages, the reservoir was filled with a concentrated drug solution. Then the solution was frozen and lyophilized to form a reservoir-bound porous drug cake.

The porous teriparatide dosages then were back-filled with one of two excipient formulations, by adding 100-125 nL of polyethylene glycol (PEG) into the reservoirs: In the first case, lyophilized PTH was back-filled with a molten solution of tartaric acid in PEG 1450. In the second case, the lyophilized PTH was back-filed with a solution (at ambient temperature) of tartaric acid in PEG 400. Tartaric acid was dissolved in PEG 1450 by incubation at 80° C. The resulting solution was dispensed using a heated syringe. More tartaric acid was dissolved in PEG 400 by stirring at room temperature. The tartaric acid content was determined by taking a minimum of 5 mL tartaric Acid in PEG and dissolving that in sufficient water to give a final volume of 150 mL. The resulting solution was titrated with 1 M NaOH.

To test the effect of the tartaric acid on teriparatide release, four reservoirs were opened and released into a phosphate buffered saline (PBS) solution (here, 10 mM sodium phosphate, 150 mM NaCl, 0.02% polysorbate 20, pH 7.3). This buffered saline recipe mimics physiological fluid in the assay. Fractions of the buffered saline solution were collected at time points. The teriparatide collected in each fraction was quantified and evaluated as a function of time.

As shown in Table 1 below, the addition of tartaric acid to the PEG markedly increased the fraction of teriparatide recovered and substantially reduced the release halftime. Release halftime is the elapsed time recovery 50% of the actual yield (not the time to recover 50% of the theoretical yield).

TABLE 1

Teriparatide Recovery and Release Halftime As a Function of Backfill Composition

| Backfill Composition | % Recovery | Release Halftime |
|---|---|---|
| PEG 400 | 61% | 17.1 hrs |
| 10% Tartaric Acid in PEG 400 | 78% | 3.8 hrs |
| PEG 1450 | 32% | >24 hrs |
| 4% Tartaric Acid in PEG 1450 | 54% | 17.3 hrs |

Figure 4:
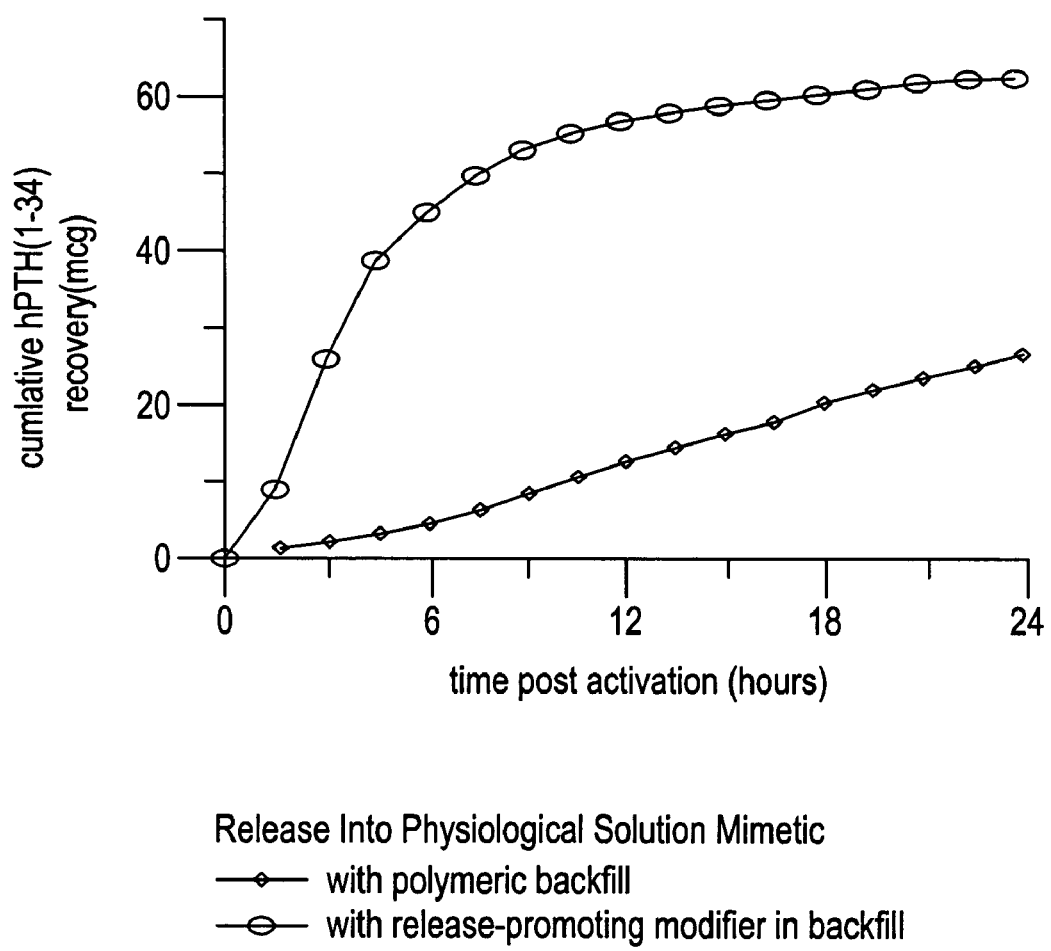
FIG. 4 is a graph of cumulative recovery of hPTH(1-34) versus time post activation of release of the drug from a reservoir array device into a physiological solution memetic, using a release promoting modifier or a polymeric back-fill in the reservoirs.

For the PEG 400 excipient mixtures, with and without tartaric acid, the cumulative recovery of teriparatide was plotted as a function of time, as shown in FIG. 4, which clearly illustrates the effectiveness of tartaric acid as a release-promoting modifier in the excipient mixture. The x-axis represents time post activation in hours and the y-axis represents cumulative teriparatide recovery in milligrams.

EXAMPLE 2

Enhanced Dissolution and Recovery of Teriparatide from a Bulk Lyophilized Cake Containing Citric Acid Solutions of teriparatide were prepared at room temperature either as a 100 mg of teriparatide per milliliter of a 25% acetic acid solution or as a 200 mg of teriparatide per milliliter of a 50% acetic acid solution. (The acid concentration is approximate, as it assumes no volumetric contribution of the teriparatide to the solution.) The teriparatide concentrations are provided as the equivalent free-base concentrations. The 200 mg/mL teriparatide solution in 25% acetic acid was subsequently diluted to 100 mg/mL teriparatide solution using a 0.4M citric acid solution to yield a solution with a teriparatide concentration of approximately 100 mg/mL, an acetic acid content of approximately 25%, and a citric acid concentration of 0.2M.

Small aliquots (20 μL) of each solution were dispensed into glass vials, frozen, and lyophilized using a conservative cycle to yield a solid cake. The expectation was that while the relatively volatile acetic acid would be removed during the lyophilization process, leaving the citric acid to remain as a component of the final lyophilized cake/drug formulation.

To test the effect of the presence of the citric acid on dissolution and recovery on the lyophilized forms, a 1 mL volume of PBS (here, a solution of 10 mM sodium phosphate, 140 mM sodium chloride, 2.7 mM potassium chloride, pH 7.4, 0.004% Tween 20) was introduced into each glass vial, containing a teriparatide lyophilized cake, with minimal agitation.

Visual observations were made about the apparent time to dissolution for each formulation. The resulting pH of the dissolution solution was also tested using pH test strips. Finally, the dissolution solutions were analyzed to quantify the tariparatide recovered from the lyophilized cake for comparison to a theoretical quantity.

As shown in Table 2 below, the inclusion of citric acid to the teriparatide formulation decreased the time required for the resultant lyophilizate to dissolve in PBS, provided a lower local pH environment, and provided a higher recovery than the lyophilizate obtained from the teriparatide formulation that did not contain citric acid.

TABLE 2

Teriparatide Dissolution and Recovery as a
Function of Primary Formulation Composition

| Stock Solvent Components | Teriparatide Concentration (mg/mL) | Dissolution Time | Measured pH (scale of 1-14) | % Recovery (average of 2) |
|---|---|---|---|---|
| 25% acetic acid | 116 | Incomplete after 20 minutes | 7 | 78 |
| 0.2M citric acid/25% acetic acid | 106 | 1-2 minutes | 5 | 103 |

These examples state concentrations of the solution components. For example, the acetic acid concentration is referenced as 25% (approximately 4 M) throughout. This concentration is approximate, as it assumes no volumetric contribution of the peptide to the solution. This assumption fails as the peptide concentration increases, resulting, in this case, in an acetic acid concentration that is something less than 25%. This point is made for clarity, although the results presented should be comparable for a range of (organic acid) concentrations around those listed in Table 2.

EXAMPLE 3

Release of Teriparatide from a Micro-reservoir
Containing Lyophilized Cake Containing Citric Acid The citric acid-containing formulations from Example 2 were dispensed (primary fill) into a device/substrate reservoirs at a volume of 200 nL per reservoir, then frozen, and then lyophilized. The % recovery in 24 hours and time to 50% release were monitored using a custom in vitro flow cell system which allows for discreet reservoirs (in this case a set of 4) to be exposed to a phosphate buffered saline (PBS) solution at 37° C. (here, a solution of 10 mM sodium phosphate, 140 mM sodium chloride, 2.7 mM potassium chloride, pH 7.4, 0.004% Tween 20). Fractions of the PBS solution were collected over time, and the teriparatide collected in each fraction was quantified for evaluation as a function of time.

Figure 5:
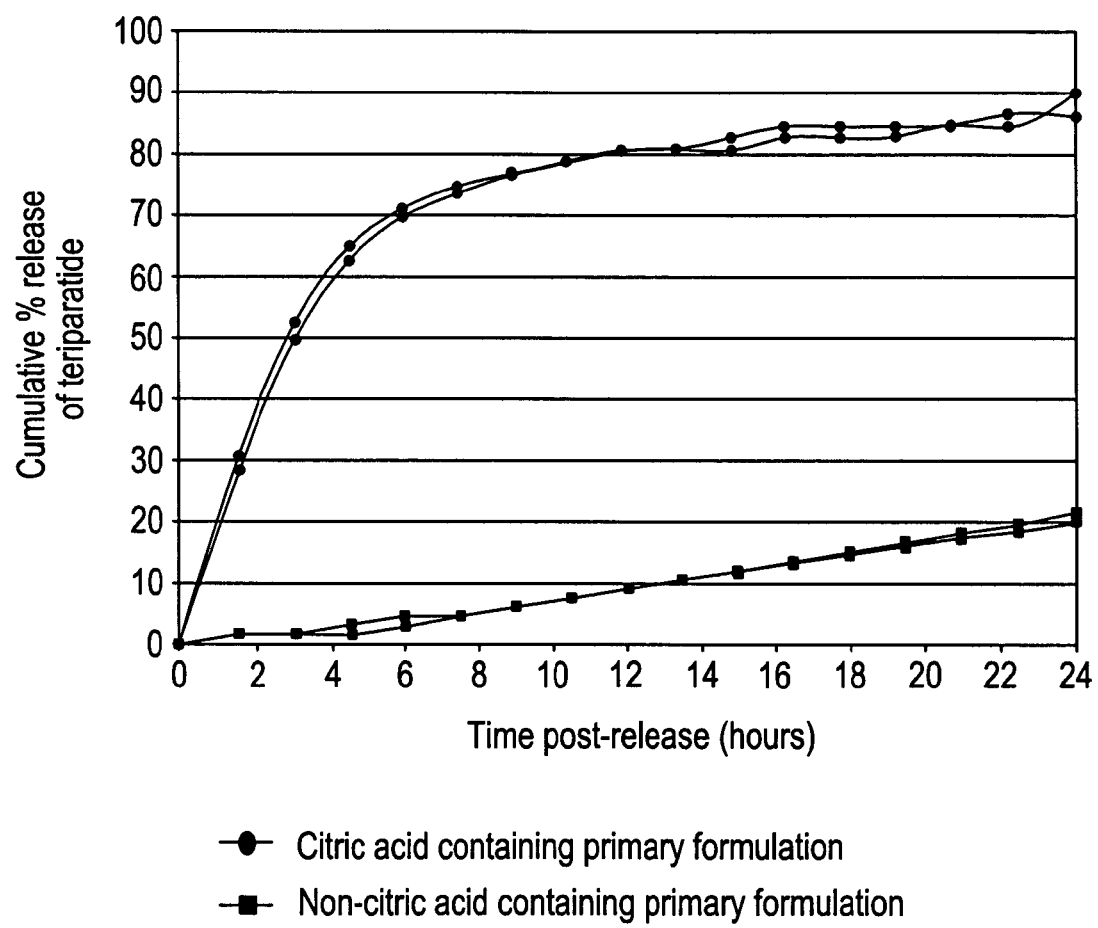
FIG. 5 is a graph of cumulative recovery of hPTH(1-34) versus time post activation of release of the drug from a reservoir array device into a physiological solution memetic, with and without citric acid as a release-promoting modifier.

As shown in Table 3, the inclusion of the citric acid in the primary fill formulation increases the total teriparatide recovery in 24 hours in neutral buffer conditions and greatly increases the time to 50% recovery from a set of discreet reservoirs. The properties observed in a neutral buffered solution, presented graphically in FIG. 5, clearly demonstrate the advantage conferred by the acid modifier on both the release rate and the cumulative recovery of hPTH(1-34).

TABLE 3

Teriparatide Recovery and Release Halftime as
a Function of Primary Formulation Composition

| Stock Solvent Components | Teriparatide Concentration (mg/mL) | % Recovery in 24 hours (average of 2) | Release Halftime (average of 2) |
|---|---|---|---|
| 25% acetic acid | 116 | 21% | >24 hrs. |
| 0.2M citric acid/ 25% acetic acid | 106 | 88% | 3 hrs. |

This example demonstrates the benefit of citric acid in the lyophilized PTH formulation on the yield and kinetics.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. An implantable medical device for the storage and controlled release of a drug formulation comprising:
   a body portion;
   at least one reservoir located in at least one surface of the body portion and having a plurality of discrete release openings;
   at least one drug formulation, which comprises at least one drug, disposed within the at least one reservoir;
   a release-modifying agent disposed within the at least one reservoir and/or within a second reservoir which is separate from the at least one reservoir in which the drug formulation is disposed, wherein the release-modifying agent is selected from the group consisting of a non-volatile, monoprotic organic acid; a non-volatile, polyprotic organic acid; a non-volatile, mono-functional base; and a non-volatile, poly-functional base;
   one or more reservoir caps closing off the plurality of discrete release openings of the at least one reservoir;
   at least one reservoir cap support between at least two of the release openings which extends over the at least one drug formulation, wherein said one or more reservoir caps are in part supported by the at least one reservoir cap support; and
   electrical circuits, a power source, and a controller for disintegrating said reservoir caps to permit release of the drug formulation from the at least one reservoir.

2. The device of claim 1, wherein the drug formulation and the release-modifying agent are both stored in the same at least one reservoir.

3. The device of claim 1, wherein the electrical circuits comprise an input lead and an output lead connected to each of said reservoir caps for disintegrating the reservoir caps by electrothermal ablation.

4. The device of claim 1, wherein the release-modifying agent enhances release of the drug formulation from said at least one reservoir to a physiological environment by inhibiting gelation, aggregation, or precipitation of the drug formulation.

5. The device of claim 4, wherein the physiological environment has a first pH, and wherein the release-modifying agent enhances release of the drug formulation from said at least one reservoir to a physiological environment by imparting a second pH to at least a portion of the physiological environment within or proximate to the at least one reservoir having the drug formulation, the second pH being less than or greater than the first pH.

6. The device of claim 1, wherein the release-modifying agent enhances release of the drug formulation from said at least one reservoir to a physiological environment by (i) altering the hydrophobic or hydrophilic nature of the physiological environment within or proximate to said at least one reservoir having the drug formulation, (ii) binding to hydrophobic or hydrophilic domains of the drug formulation, or (iii) inhibiting oxidation of the drug formulation in the physiological environment.

7. The device of claim 2, wherein the drug formulation is in the form of a solid matrix having pores or interstices.

8. The device of claim 7, wherein the release-modifying agent enhances dissolution of the drug formulation into a physiological liquid by increasing the capillary action of the physiological liquid through the matrix solid or by causing the solid matrix to be crystalline.

9. The device of claim 7, wherein the release-modifying agent is located into the pores or interstices of the solid matrix.

10. The device of claim 7, further comprising one or more excipient materials, wherein the release-modifying agent and the one or more excipients materials are located in the pores or interstices of the solid matrix.

11. The device of claim 10, wherein at least one of the one or more excipient materials is in solid form.

12. The device of claim 10, wherein at least one of the one or more excipient materials comprises a polyethylene glycol or another polymeric material.

13. The device of claim 1, wherein the at least one reservoir further comprises a void volume displacing material.

14. The device of claim 1, wherein the drug formulation is sealed in the at least one reservoir at a reduced pressure, relative to ambient pressure, or with an inert gas, or both at a reduced pressure and with an inert gas.

15. The device of claim 2, wherein the release-modifying agent is provided in the at least one reservoir in the form of one or more first layers and the drug formulation is provided in the at least one reservoir in the form of one or more second layers adjacent to and/or interspersed with the one or more first layers.

16. The device of claim 2, wherein the drug formulation and the release-modifying agent are in the form of a molten solution or suspension.

17. The device of claim 1, wherein the at least one reservoir is a microreservoir.

18. The device of claim 1, having a plurality of discrete reservoirs provided in an array on a surface of the body portion and containing the drug formulation.

19. The device of claim 1, wherein the body portion is in the form of a chip, a disk, a tube, or a sphere.

20. The device of claim 1, wherein the body portion comprises silicon, a metal, a polymer, a ceramic, or a combination thereof.

21. The device of claim 1, wherein the drug formulation comprises an amino acid, a peptide, or a protein.

22. The device of claim 1, wherein the release-modifying agent comprises citric acid.

23. The device of claim 1, wherein the drug formulation comprises human parathyroid hormone, a leutenizing hormone-releasing hormone, a gonadotropin-releasing hormone, a natriuretic peptide, exenatide, pramlintide, a tumor necrosis factor (TNF) inhibitor, an analog thereof, or a combination thereof.

24. The device of claim 1, wherein the release-modifying agent comprises at least one non-volatile, monoprotic or polyprotic organic acid.

25. The device of claim 1, wherein the release-modifying agent comprises at least one non-volatile, mono- or polyfunctional base.

26. The device of claim 1, wherein the volume of the at least one reservoir is between 1 nL and 500 µL.

27. An implantable medical device for the storage and controlled release of a drug formulation comprising:
a body portion;
a plurality of discrete reservoirs located in at least one surface of the body portion, each reservoir having two or more release openings;
at least one drug formulation, which comprises a drug, disposed within at least a portion of the plurality of discrete reservoirs;
a plurality of discrete reservoir caps closing off the release openings of each of the reservoirs;
a reservoir cap support between said two or more release openings which extends over the at least one drug formulation, wherein at least two of said discrete reservoir caps are in part supported by the at least one reservoir cap support;
activation means for selectively disintegrating two or more of the reservoir caps to permit release of the drug formulation from one of the plurality of discrete reservoirs;
a release-modifying agent disposed within the at least a portion of the plurality of discrete reservoirs, wherein the release-modifying agent is selected from the group consisting of a non-volatile, monoprotic organic acid; a non-volatile, polyprotic organic acid; a non-volatile, mono-functional base; and a non-volatile, poly-functional base.

28. The device of claim 27, wherein the release-modifying agent comprises citric acid.

29. The device of claim 27, wherein the drug formulation comprises human parathyroid hormone, a leutenizing hormone-releasing hormone, a gonadotropin-releasing hormone, a natriuretic peptide, exenatide, pramlintide, a tumor necrosis factor (TNF) inhibitor, an analog thereof, or a combination thereof.

30. The device of claim 27, wherein the drug formulation is in the form of a solid matrix having pores or interstices.

31. The device of claim 30, wherein the release-modifying agent is located within the pores or interstices of the solid matrix.

32. The device of claim 30, further comprising one or more excipient materials located in the pores or interstices of the solid matrix.

33. The device of claim 32, wherein at least one of the one or more excipient materials is in solid form.

34. The device of claim 32, wherein at least one of the one or more excipient materials comprises a polymeric material.

35. The device of claim 34, wherein the one or more excipient materials comprises a polyethylene glycol.

36. The device of claim 27, wherein the drug formulation is sealed in the plurality of discrete reservoirs at a reduced pressure relative to ambient pressure, with an inert gas, or both at a reduced pressure and with an inert gas.

37. The device of claim 27, wherein the volume of each discrete reservoir is between 1 nL and 500 µL.

38. An implantable medical device for the storage and controlled release of a drug formulation comprising:
a body portion;
a plurality of discrete microreservoirs located in the body portion, each reservoir having two or more discrete release openings separated by a reservoir cap support;
a drug which comprises a protein or peptide, disposed within each of the plurality of discrete microreservoirs, wherein the drug is in a lyophilized porous solid form; and
a release-modifying agent which comprises a non-volatile, water soluble organic acid or conjugate base, the release modifying agent being disposed with the drug within each of the plurality of discrete microreservoirs.

39. The implantable medical device of claim 38, wherein the water soluble organic acid is selected from the group consisting of citric acid, acetic acid, succinic acid, fumaric acid, pivalic acid, lactic acid, tartaric acid, amino acids, and combinations thereof.

40. The implantable medical device of claim 38, wherein the water soluble organic acid is mixed with the drug in the lyophilized porous solid form.

41. The implantable medical device of claim 40, wherein each of the plurality of microreservoirs further comprises a void volume displacing material infiltrating the pores of the lyophilized porous solid form.

42. The implantable medical device of claim 38, further comprising:

a plurality of discrete reservoir caps closing off said plurality of discrete release openings; and electrical circuitry, a power source, and a controller for selectively disintegrating each of the reservoir caps to permit release of the drug formulation from the microreservoirs.

43. The implantable medical device of claim 38, wherein the body portion comprises two or more substrate portions bonded together, one of said substrate portions comprising the at least one reservoir cap support.

* * * * *